United States Patent
Tanikawa

(10) Patent No.: US 7,827,850 B2
(45) Date of Patent: Nov. 9, 2010

(54) GAS-LIQUID TWO-PHASE FLOW CHROMATOGRAPHIC ANALYZER AND METHOD OF ANALYSIS USING THE SAME ANALYZER

(75) Inventor: Isao Tanikawa, Yokohama (JP)

(73) Assignee: Tokyo Seikan Kaisha, Ltd., Tokyo (JP)

( * ) Notice: Subject to any disclaimer, the term of this patent is extended or adjusted under 35 U.S.C. 154(b) by 642 days.

(21) Appl. No.: 11/910,045

(22) PCT Filed: Mar. 31, 2006

(86) PCT No.: PCT/JP2006/307413
§ 371 (c)(1),
(2), (4) Date: Sep. 28, 2007

(87) PCT Pub. No.: WO2006/104286
PCT Pub. Date: Oct. 5, 2006

(65) Prior Publication Data
US 2009/0249860 A1    Oct. 8, 2009

(30) Foreign Application Priority Data
Mar. 31, 2005    (JP) .............................. 2005-100573

(51) Int. Cl.
*G01N 1/00* (2006.01)
(52) U.S. Cl. .................................... 73/23.41
(58) Field of Classification Search ................. 73/23.41
See application file for complete search history.

(56) References Cited

U.S. PATENT DOCUMENTS 5,235,843 A    8/1993 Langhorst

2005/0087122 A1    4/2005 Ismagliov et al.

FOREIGN PATENT DOCUMENTS

| JP | 59-141064 | 8/1984 |
|----|-----------|--------|
| JP | 9-68522 | 3/1997 |
| JP | 2004-333270 | 11/2004 |

(Continued)

OTHER PUBLICATIONS

R.C. Fernandes, et al.; "Hydrodynamic Model for Gas-Liquid Slug Flow in Vertical Tubes"; AIChE Journal (vol. 29, No. 6); Nov. 1983; pp. 981-989; XP002507397.

(Continued)

*Primary Examiner*—Hezron Williams
*Assistant Examiner*—Alex Devito
(74) *Attorney, Agent, or Firm*—Sughrue Mion, PLLC

(57) ABSTRACT

This invention provides a chromatographic apparatus comprising an introduction part for a carrier gas as a main mobile phase medium, a sample injection part, a separation column comprising a stationary phase formed by coating a polymeric material, a part for housing the separation column, and a detector. The sample injection part is provided between the carrier gas introduction part and the inlet of the separation column. The chromatographic apparatus further comprises a solvent introduction means for adding a liquid solvent as a second mobile phase medium to a carrier gas and mixing them together, a mechanism for regulating the amount of the carrier gas introduced and the amount of the solvent added, and a mechanism for regulating the temperature of each flow passage. A plurality of clogging liquid stoppers, of which the liquid film thickness is equal to the inner diameter of a capillary column, are partly provided at predetermined intervals within the column in a longitudinal direction of the column. In such a state that a gas phase and a liquid phase are intermittently alternated, a mobile phase medium is moved toward a column outlet and a sample is separated by utilizing distribution between the solvent liquid film of the mobile phase medium and the column stationary phase. There is also provided a chromatographic analytical method utilizing this apparatus. According to this method, a sample can be separated without using any high pressure pump.

16 Claims, 23 Drawing Sheets

FOREIGN PATENT DOCUMENTS

WO          98/02237   A1     1/1998
WO     2004/087283   A1    10/2004

OTHER PUBLICATIONS

T.C. Thulasidas, et al.; "Dispersion during bubble-train flow in capillaries"; Chemical Engineering Science; vol. 54, No. 1; Jan. 1999; pp. 61-76; XP002507396.

W.L. Chen, et al.; "Gas-liquid two-phase flow in micro-channels"; International Journal of Multiphase Flow; vol. 28, No. 7; Jul. 2002; pp. 1235-1247; XP002507395.

Z. Luo, et al.; "Chromatography With Dynamically Created Liquid "Stationary" Phases: Methanol and Carbon Dioxide", Anal. Chem., American Chemical Society, Jul. 15, 2003, vol. 75, Num. 14, pp. 3557-3562.

SLUG FLOW   FROTH FLOW   HUGE WAVE FLOW   ANNULAR FLOW

TIME [s]

| VOID FRACTION | HOLDUP FRACTION | NAME OF FLOWS |
|---|---|---|
| 990 | 0.009 | ANNULAR FLOW |
| 985 | 0.015 | |
| 970 | 0.030 | HUGE WAVE FLOW ↓ |
| 960 | 0.040 | |
| 940 | 0.060 | FROTH FLOW ↓ |
| 909 | 0.081 | |
| 870 | 0.130 | |
| 769 | 0.231 | SLUG FLOW ↓ |
| 625 | 0.375 | |
| 500 | 0.500 | |

(A) RESIN $\delta - \gamma c$ CORRELATION
$y = 2.6086x - 1.7864$ (B)

GC-WATER FILM CONVERSION/LOW-BOILING MINERAL OIL-AROMATIC MIXTURE

COLUMN: DB1701 1μDp 0.25mm—50M

UPPER: HEXANE SOLUTION IS INJECTED 50-120°C

LOWER: 5 MIN. AFTER COOLED TO 50°C, 1μL OF WATER IS INJECTED WATER IS ADDED AT 04μL PER MIN.

TEMP. ELEVATED: 50−280°C/10°C

WATER FILM GC-GC CONVERSION/POLYHYDRIC
ALCOHOL-AROMATIC · PARAFFIN MIXTURE
COLUMN:AQUATIC 1μDp 0.25mm-60M
  UPPER:AFTER ACETONE SOLUTION ON-COLUMN INJECTION AND DRYING,
    WATER IS CONTINUOUSLY INJECTED AT 05μL PER MIN.
    50°C 3 MIN.-80°C 5 MIN. -120°C CONST.
  LOWER:AFTER HAVING STOPPED FEEDING WATER, WATER IS DRAINED AT
    50°C-TEMP IS ELEVATED TO 280°C/15°C PER MIN.

(a)

(b)

WATER FILM/GAS-LIQUID TWO-PHASE FLOW COMPOSITE CHROMATOGRAPHY IN A NARROW BORE DB1701-3M SHORT COLUMN

COLUMN:DB1701 0.1mmΦ-3MDf1.0
WITHOUT ULTRASONIC WAVES (a) 50°C CONST/ AQ. SOLUTION 0.5 μL He;0.8ml (b) 50°C CONST 60 MIN.

(c) TEMP IS ELEVATED TO 50°C-250°C WATER/OFF

EFFECT OF ULTRASONIC WAVES USING THE GAS-LIQUID TWO-PHASE FLOW CHROMATOGRAPHY

COLUMN DB1701 0.25φ 3M
TNP ON-COLUMN INJECTION, ULTRASONIC VIBRATION

ULTRASONIC GENERATOR
39KHz, 100W (a)

(b)

(a)

(b)

(A)

SEPARATION OF HIGHER FATTY ACIDS BY THE POLYSTYRENE CAPILLARY COLUMN 0.1mm$\phi$ -10M He:0.1mL/MIN. WATER 0.5$\mu$L/MIN.
ESTIMATED WATER FILM THICKNESS:0.5$\mu$m (B)

SEPARATION OF HIGHER FATTY ACIDS BY THE POLYSTYRENE CAPILLARY COLUMN (ENLARGED DIAGRAM)

GAS-LIQUID TWO-PHASE FLOW CHROMATOGRAPHIC ANALYZER AND METHOD OF ANALYSIS USING THE SAME ANALYZER

BACKGROUND ART

The present invention relates to a gas-liquid two-phase flow chromatographic analyzer and to a method of analysis using the same analyzer. More specifically, the invention relates to a chromatographic analyzer based on a novel principle which makes it possible to separate and develop sample components maintaining a very high resolving power even when a sample to be analyzed contains sparingly volatile components by using a carrier gas as a first mobile phase medium and a liquid solvent such as water as a second mobile phase medium, and by forming a gas-liquid two-phase flow of a particular state in a open tubular separation column. The invention, further, relates to a method of chromatographic analysis capable of easily separating and developing a sample containing a variety of easily volatile through up to sparingly volatile components by using the above analyzer.

BACKGROUND ART

A high-performance liquid chromatography (HPLC) is usually used for separating and analyzing sparingly volatile or non-volatile components which are difficult to be analyzed by a gas chromatography (GC). The high-performance liquid chromatography has now been widely used for analyzing trace amounts of components in a variety of chemical fields, for analyzing the environment, for developing pharmaceuticals and for controlling qualities.

For the HPCL, there have heretofore been demanded to shorten the time for analysis, analyze the same of even a very small amount, and improve separation performance, as well as to decrease the size of the apparatus and to decrease the weight. To meet these demands, a number of proposals have heretofore been made concerning the liquid feed pump in the apparatus, decreasing the size of flow-path parts, decreasing the weight thereof, use of a separation column of a small diameter, improving the column efficiency and so on.

For example, JP-A-2003-107064 discloses an invention of a liquid feeding system for a high-performance liquid chromatograph which is compact, is of a low cost and is of the type of saving energy, JP-A-2005-257017 discloses an invention of a micro valve, and JP-A-2004-037266 discloses an invention for improving the efficiency of a separation column.

In recent years, in particular, liquid chromatographic apparatuses that feed the liquid in very small amounts have been vigorously studied by applying a high-speed and small-diameter separation column (micro column), and quite a few of them are utilizing a highly sophisticated and expensive system such as LC-MS/MS.

To attain the analysis at a higher speed and to improve the separation performance of the liquid chromatographic apparatus that feeds the liquid in very small amounts, however, it becomes necessary to increase the theoretic number of plates of the separation columns, to minimize the dead volume in the sample injection portion and in the flow path to minimize the diffusion of the sample components after the injection until arriving at the detection portion.

Therefore, efforts have been made to minimize the dead volume in the connection paths and in the valves. Concerning the micro columns, too, efforts have been made to improve the separation efficiency by further decreasing the diameter and by using a column packing of fine particles.

DISCLOSURE OF THE INVENTION

However, the conventional valve type injection devices used in these apparatuses use flow paths of volumes in a unit of μL, causing a serious decrease in the separation capability in the liquid chromatographic analysis that feeds the liquid at such a small rate as 10 μL/min. or less.

To improve this, at present, a method has been employed for conveying part of a very small flow path in a form substituted by a sample solution to the separation column maintaining its shape, which, however, is not still satisfactory requiring a change-over valve provided with a micro volume flow path and syringe pump for feeding the liquid in small amounts, and still leaving problems such as cumbersome structure and cumbersome handling operation.

To increase the theoretical number of plates of the separation columns, further, the size of the column packing particles must be decreased or the length of the column must be increased requiring, however, a very high pressure for maintaining a certain degree of velocity of flow of the mobile phase medium (developer), and making it necessary to select a material that withstands the high pressure and to form the pressure-resistant structure without substantially dead volume.

This can be completely achieved requiring, however, laborious work and high cost.

A first object of the present invention is to provide a gas-liquid two-phase flow chromatographic analyzer which features the separation and resolving power which are strikingly higher than those of the HPLC, and is capable of completely analyzing the samples containing sparingly volatile components under a low pressure and at a high speed comparable to those of general gas chromatographic apparatuses, relying upon a chromatographic principle quite different from the traditional principle, i.e., relying upon a quite novel chromatographic principle of using a carrier gas and a liquid solvent as a mobile phase media, moving the mobile phase toward the outlet of the column in a state where a gas-liquid two-phase flow is formed in a particular state in which the gas phase and the liquid phase are intermittently alternating in the separation column, and conducting the separation and developing by utilizing the distribution of the solvent membrane and the column solid phase.

A second object of the present invention is to provide a composite chromatographic analyzing method capable of directly analyzing the samples containing a variety kinds of easily volatile through up to sparingly volatile or nonvolatile components by using the above gas-liquid two-phase flow chromatographic analyzer and, for example, a water membrane gas chromatographic apparatus developed and proposed already by the present inventors (see JP-A-2004-333270) in combination, or by using a single apparatus capable of executing the above two chromatographic analyses.

According to the present invention, there is provided a gas-liquid two-phase flow chromatographic apparatus for the chromatographic analysis using a carrier gas as a main mobile phase medium and a polymer which is not miscible with water as a solid phase, and comprising at least a carrier gas introduction portion, a sample injection portion, a capillary column having a layer of the solid phase formed on the inner peripheral walls thereof, a container portion thereof and a detection portion; wherein the sample injection portion is provided between the carrier gas introduction portion and the inlet of the capillary column, and includes medium introduction means capable of adding and mixing a liquid solvent as a second mobile phase medium to the carrier gas, a mechanism for controlling the amount of introducing the carrier gas and the amount of adding the mobile phase solvent, and a mechanism for controlling the temperatures of the flow paths in which the two mobile phase media come in contact; and wherein the analyzer is so constituted that the portions of the apparatus and the control mechanism are interlinked together in a manner that the liquid membrane thickness partly forms a plurality of manometric liquid plugs in the separation column which is in operation in the radial direction of the capillary and in the lengthwise direction of the column maintaining an interval, that the mobile phase media move toward the outlet of the column in a state where the gas phase and the liquid phase are intermittently alternating, and that the chromatographic analysis is conducted while executing the separation and developing by utilizing the distribution of the solvent membrane of the mobile phase media and the column solid phase.

The above chromatographic apparatus of the present invention has a feature in the use of two kinds of mobile phase media, i.e., a carrier gas (gaseous phase) and a liquid solvent such as water (liquid phase), wherein the liquid membrane of the solvent phase partly forms a plurality of intermittent manometric liquid plugs nearly regularly in the separation column which is in operation in the radial direction of the capillary and in the lengthwise direction in the column, the mobile phase media are moved toward the outlet of the column in a state where the gas phase and the liquid phase are intermittently alternating, and the separation and developing are conducted by utilizing the distribution of the solvent liquid phase and the column solid phase. In this specification will appear the expressions using water and liquid, such as liquid membrane and water membrane, as well as liquid mass and water mass. When water is used as the solvent, the words become water membrane and water mass, and when any other organic solvent is used, the words become liquid membrane and liquid mass, without any difference in the technical meaning.

In the above apparatus, the mobile phase medium is not moved by a high compression pump that is employed for the high-performance liquid chromatographic apparatus (HPLC), and a very small pressure loss is caused by the passage through the column. Besides, the apparatus does not have to withstand high pressures. That is, the apparatus does not have to be highly pressure resistant due to the employment of a liquid feed system that utilizes the static pressure of the carrier gas like the gas chromatographic apparatus (GC).

Further, the solvent membrane separated in the alternating gaseous phase forms plugs (disk-like liquid masses) of a very small volume, and the diffusion and mixing in the separation field are substantially avoided, which was a serious factor detrimental for obtaining a high separation capability in the case of the HPLC, making it possible to obtain a very large number of theoretical plates.

In order to achieve a preferred gas-liquid two-phase flow chromatographic analysis, i.e., to favorably separate and develop the sample components by using the apparatus of the present invention, it is desired that the solvent membrane in the capillary column in the apparatus which is in operation has an average value of the estimated liquid membrane thickness in a unit time (1 unit: shorter than 10 seconds) in a range of not smaller than 0.1 µm as calculated according to the following formula (1), Average value (µm) of the estimated liquid membrane thickness in a unit time=inner diameter of column (mm)×(1−α)×10³ (1)

wherein α is a ratio represented by (flow rate of gaseous volume/flow rate of the volume of the whole fluid) of the fluid in the capillary column under the atmospheric pressure, and is technically called void fraction.

The upper limit of the estimable water membrane thickness cannot be specified since it varies depending upon the permissibility of a mass analyzer which is a detector for a decrease in the degree of vacuum. The upper limit, however, is 1.0 µm in the case of the capability of a vacuum pump in the apparatus used by the present inventors.

It is further desired that a wet contact angle between the liquid solvent which is the second mobile phase medium and the solid phase material in the capillary column is not smaller than 77°.

It is further desired that the liquid solvent is water, and the solid phase material in the capillary column is a high molecular resin or a resin composition having a solubility parameter value of not higher than 18.3 $MPa^{1/2}$, or is the one of which the surfaces are so treated as to exhibit surface property of a solubility parameter value of not higher than 18.3 $MPa^{1/2}$.

As a liquid solvent other than water, it is desired to use a water/organic solvent mixed solution, an organic solvent or an organic solvent-mixed solution having a wet contact angle of not less than 77° relative to the solid phase material.

In the apparatus of the present invention, it is desired that the solvent introduction means which adds and mixes the solvent as the second mobile phase medium to the carrier gas, works to heat, vaporize and continuously introduce the solvent at an average liquid flow rate of 0.01 to 2 µL/min. and, thereafter, condense and liquefy the solvent, so that a state of a two-phase flow of mobile phase media in which the gas and the liquid are intermittently alternating is established in the capillary column in which an average value of the estimated liquid membrane thickness in a unit time is in a range of 0.1 to 1.0 µm, or the solvent introduction means continuously introduces the solvent at an average liquid flow rate of 0.01 to 2 µL/min. by using a liquid feed pump, so that a state of a two-phase flow of mobile phase media in which the gas and the liquid are intermittently alternating is established in the capillary column in which an average value of the estimated liquid membrane thickness in a unit time is in a range of 0.1 to 1.0 µm.

Further, means that establishes a state of a two-phase flow of mobile phases in which the gas and the solvent are intermittently alternating in the capillary column, is a tubular flow path which introduces the carrier gas from one end thereof and introduces the solvent or the carrier gas containing the vapor thereof from the other end thereof, the end on the outlet side of the confluent path thereof being connected to the separation column, and the tubular flow path is further provided with a capillary portion of an inner diameter small enough to be closed by the liquid solvent or the condensate of the solvent vapor that is introduced, the tubular flow path further having a solvent flow rate adjusting mechanism for alternately repeating a step of forming closing membranes or masses of the solvent introduced into the capillary portion and a step of eliminating the closing by conveying the closing portions with the carrier gas, and a carrier gas flow rate-adjusting mechanism, wherein the alternating interval is adjusted by the cooperative operations thereof to realize the state of two-phase flow of mobile phase media in which the gas and the liquid are intermittently alternating.

It is desired that the apparatus is further provided with a mechanism that gives sonic vibration to the capillary column.

It is further desired that the apparatus of the invention uses a mass analyzer as the detector and/or a hydrogen flame ionization detector as the detector.

It is further desired that the apparatus of the invention uses, as the solid phase in the separation column, a styrene resin and a polyisobutylene resin, an olefin resin having a branched methyl group, such as a 4-methylpentene resin, or a three-dimensionally crosslinked product thereof.

According to the present invention, there is further provided a composite chromatographic analyzing method using a carrier gas as a main mobile phase medium and a polymer which is not miscible with water as a solid phase by using a chromatographic analyzer comprising at least a carrier gas introduction portion, a sample injection portion, a capillary column having a layer of the solid phase formed on the inner peripheral walls thereof, a container portion thereof, a detection portion and means capable of adding water, water vapor or an organic solvent to the carrier gas, the composite chromatographic analyzing method comprising the steps of:

A) introducing a gas comprising chiefly the carrier gas into the capillary column to separate and develop volatile components in a sample to be analyzed that is injected in a gas-solid gas chromatographic state;

B) separating and developing chiefly polar component materials by adding and mixing a predetermined amount of water, water vapor or both of them to the carrier gas so as to form a water membrane of nearly a constant thickness having an average value of the estimated liquid membrane thickness in a unit time of 0.01 to 0.09 μm on the surface of the solid phase in the capillary column; and C) separating and developing the component materials that are difficult to be separated and developed in the steps A) and B) above by adding and mixing a predetermined amount of liquid solvent capable of forming a solvent membrane of an average value of the estimated liquid membrane thickness in a unit time of not less than 0.1 μm in the separation column as a second mobile phase medium to the carrier gas which is the first mobile phase medium, and by moving the mobile phase media toward the outlet of the column in a state where the solvent membrane is partly forming a plurality of manometric liquid plugs in the radial direction of the capillary column and in the lengthwise direction in the column maintaining an interval in the separation column, the gas phase and the liquid phase intermittently alternating.

The composite chromatographic analyzing method of the present invention has a feature in the combination of the gas-solid gas chromatographic analysis, water membrane gas chromatographic analysis, and the gas-liquid two-phase flow chromatographic analysis using the apparatus of the present invention.

This makes it possible to analyze at one time mixed samples containing various kinds of components, i.e., containing volatile materials which are gaseous at normal temperature, polar materials, sparingly volatile materials without having eutectic system with the solvent, and polymers such as oligomers which are not substantially volatile without the need of conducting any particular complex pretreatment.

The water membrane gas chromatographic analysis has been described in detail in JP-A-2004-333270, according to which a water membrane of a very small but nearly steady thickness is formed on the surface of the solid phase in the capillary column to conduct the analysis. This helps move and develop the sample components relying on the condensation or vaporization of water in the separation column, and is particularly effective in separating and developing the polar component materials.

The analyzer used for the above method, usually, uses two apparatuses, i.e., a water membrane gas chromatographic apparatus capable of conducting the gas-solid gas chromatographic analysis and the water membrane gas chromatographic analysis at one time, and the apparatus of the invention capable of effecting the gas-liquid two-phase flow chromatographic analysis. However, it is also allowable to separately use three apparatuses for the gas-solid, water membrane and gas-liquid two-phase flow, or to use a single apparatus incorporating the above three chromatographic analyses.

As described above, the gas-liquid two-phase flow chromatographic analyzer of the present invention is based on a novel chromatographic principle which is quite different from conventional principle, i.e., is based on a novel principle of using a carrier gas and a liquid solvent are as mobile phase media, moving the mobile phase toward the outlet of the column under a static pressure of the carrier gas in a state where a gas-liquid two-phase flow is formed in a particular state with the gas phase and the liquid phase intermittently alternating in the separation column, and conducting the separation and development by utilizing the distribution of the solvent membrane and the column solid phase. Therefore, the pressure loss in the separation column is close to the pressure loss in the gas chromatographic apparatus, and can be very decreased compared to that of the existing high-performance liquid chromatography (HPLC).

Therefore, the length of the separation column can be very increased and, besides, the manometric solvent membrane for separating the gas-liquid phase has a very small volume, substantially avoiding the diffusion and mixing in the separation field, which was a serious factor against obtaining a high separation performance with the HPLC, and markedly increasing the number of theoretical-plates per a unit column length.

Therefore, the separation capability is very high for the sample components. Besides, the motion of the mobile phase media is not based on a high compression pump used in the HPLC but is based on a static gaseous pressure like in the gas chromatographic apparatus (GC). Therefore, a very small pressure loss is caused by the passage-through the column, the apparatus does not require a high pressure resistant structure, and the samples containing sparingly-volatile components can be completely analyzed under a pressure and maintaining a high speed comparable to those of general gas chromatographic apparatuses.

Upon combining the gas-solid gas chromatographic analysis, water membrane gas chromatographic analysis and the gas-liquid two-phase flow chromatographic analysis using the apparatus of the invention, the composite chromatographic analyzing method of the invention makes it possible to analyze at one time the samples containing various kinds of components, i.e., containing volatile materials which are gaseous at normal temperature, polar materials, sparingly volatile materials without having eutectic system with the solvent, and polymers such as oligomers which are not substantially volatile without the need of conducting any particular complex pretreatment.

BEST MODE FOR CARRYING OUT THE INVENTION

Figure 1:
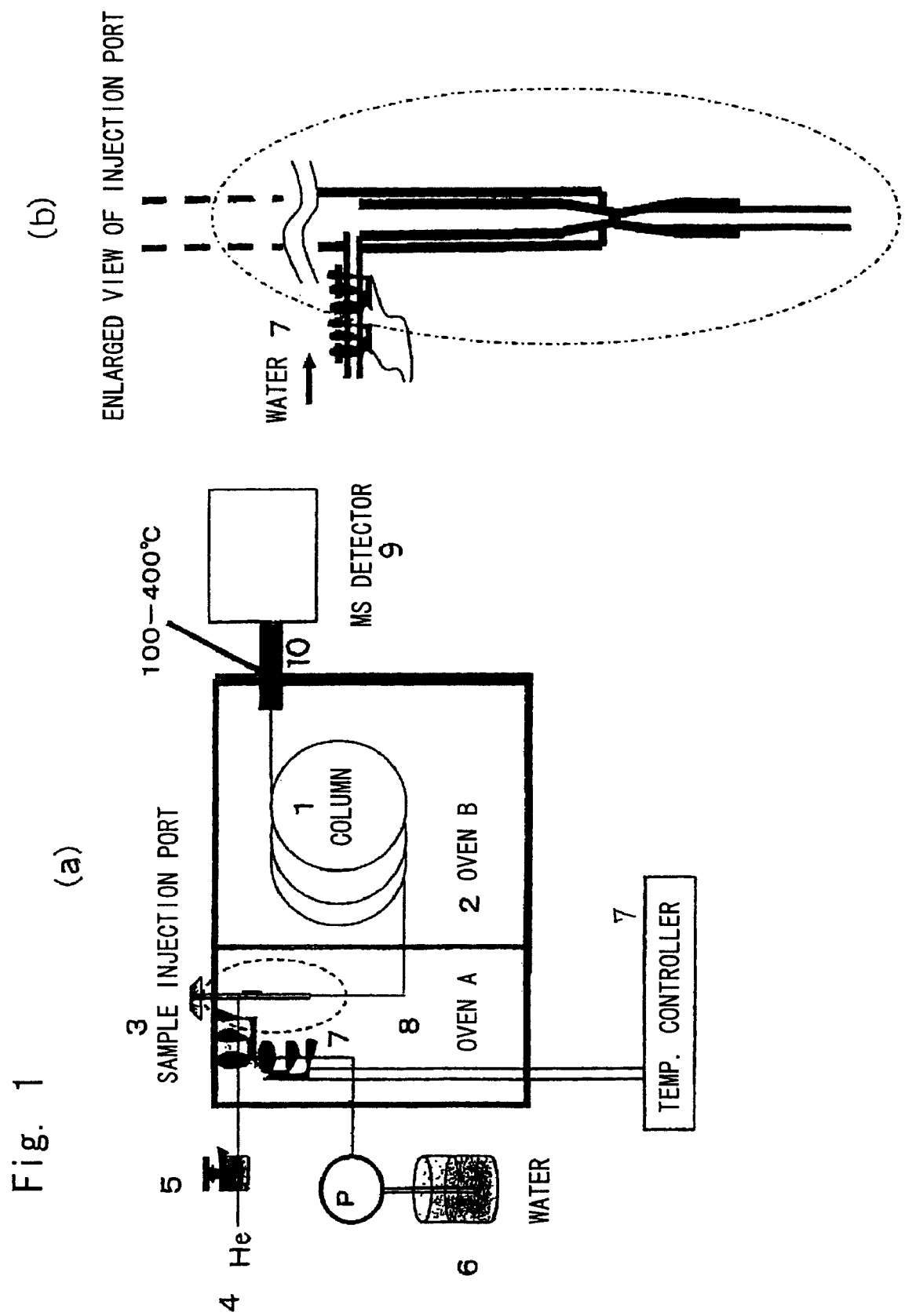
FIG. 1 includes a schematic diagram (a) of a gas-liquid two-phase flow chromatographic analyzer of the present invention and a diagram (b) partly illustrating, on an enlarged scale, a sample injection port thereof.

First, described below is the basic constitution of a gas-liquid two-phase flow chromatographic apparatus according to the present invention.

FIG. 1(a) is a diagram schematically illustrating an embodiment of the gas-liquid two-phase flow chromatographic analyzer of the present invention, wherein reference numeral 1 denotes a capillary column, 2 denotes a container portion (oven B) with a temperature-adjusting mechanism for the column, 3 denotes a sample injection port, 4 denotes a tank (not shown) filled with a carrier gas such as He, Ar, nitrogen or the like, 5 denotes a pressure governor, 6 denotes a heated bubbling water tank, 7 denotes a temperature controller for maintaining the state of water vapor, 8 denotes a container portion (oven A) with a temperature-adjusting mechanism for the inlet portion of the capillary column 1, reference numeral 9 denotes a mass analyzer working as a detector portion, and reference numeral 10 denotes a mechanism such as a heating portion or a nebulizer for introducing high-boiling or nonvolatile components into an ion source.

FIG. 1(b) is a diagram illustrating, partly on an enlarged scale, the structure near the sample injection port in the apparatus of FIG. 1(a).

Though not wholly diagramed, the apparatus of FIG. 1 is provided with temperature control means capable of adjusting the temperatures of water or solvent introduction portion, carrier gas introduction portion, sample injection port and a flow path portion of the separation column where the mobile phase medium comes in contact, and is, further, provided with a flow-rate or pressure adjusting valve for adjusting the flow rate of the carrier gas or the solvent vapor, as well as control mechanism (not shown) for controlling them being linked thereto.

The apparatus shown in FIG. 1 uses water as the second mobile phase medium (liquid solvent). The second mobile phase medium (water) is fed from the bubbling tank in the state of water vapor being mixed into part of the carrier gas, and is, further, mixed into the remainder of the carrier gas so as to be introduced into the system through near the sample injection port (see FIG. 1(b)).

The apparatus of the invention is not limited to the embodiment shown in FIG. 1 only but may be of an embodiment in which the liquid solvent is directly introduced into the system using a liquid feed pump or the like, as a matter of course.

As the liquid feed pump, there can be used various kinds of micro feeders such as those of the plunger type, syringe type or gaseous pressure type. Particularly preferably, there can be used the one of the micro syringe type for the capillary HPLC.

Figure 2:
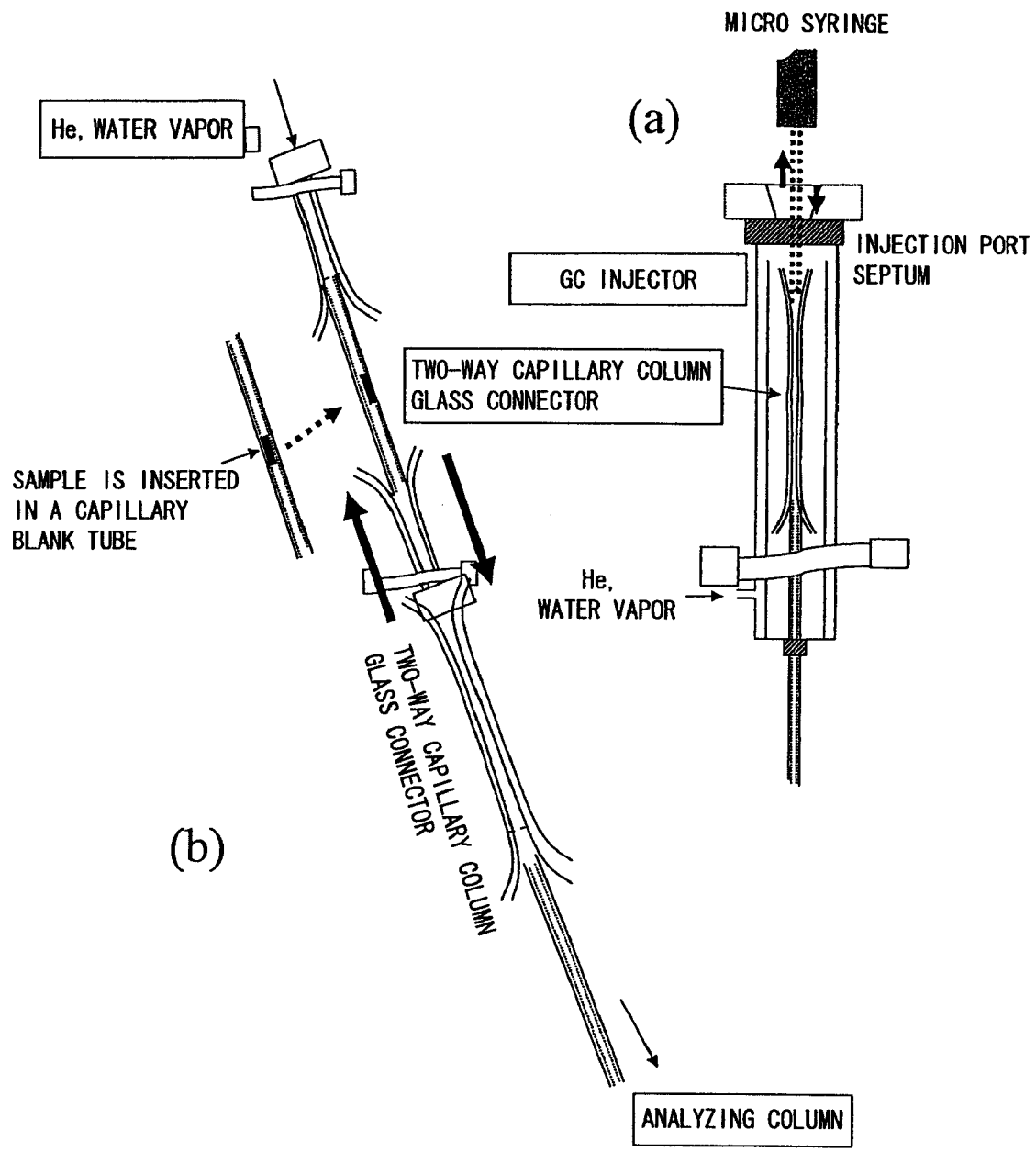
FIG. 2 is a view schematically illustrating an embodiment of on-column-injecting a sample into a capillary column, wherein (a) illustrates an embodiment of an injector and (b) illustrates an embodiment of a capillary pipe.

The samples to be analyzed in many cases contain high-boiling sparingly volatile components. According to the present invention, therefore, the sample injection port of the apparatus is preferably of a structure in which the sample is inserted in the system through an injection port septum by using a micro syringe as shown in FIG. 2(a) or of a structure in which the sample is inserted in the system by using a capillary tube filled with the sample as shown in FIG. 2(b). A more preferred injection portion will be realized if nano flow path injectors for injecting the samples become available in the market.

The capillary column used in the apparatus of the invention is the one obtained by depositing a polymer which is not miscible with water that is a solid phase on the inner wall of the column in the form of a homogeneous layer.

The column diameter is, usually, about 0.10 to 0.6 mm and, particularly preferably, 0.1 to 0.25 mm.

The column length is not particularly limited and may, often, be as long as 100 meters or more. Usually, however, the column length is about 1 to 60 meters. There is no particular limitation, either, on the column materials. There can be used materials usually used for the GC and HPLC, such as tubes of a glass, quartz and a stainless steel.

The solid phase material according to the present invention is also selected from a relationship to the properties of the second mobile phase medium (liquid solvent) as will be described later in detail.

As the detector used in the detecting portion, there have been chiefly used mass analyzers (MS) of the type of magnetic field and of the quadrupole type, and a detector of the hydrogen flame ionization type (FID).

The MS detector used for the HPLC is of the type of electron spray ionization (ESI), high-speed ion bombardment ionization (FAB), atmospheric pressure ionization (API) or chemical ionization (CI).

These ionization methods are soft ionization methods which can easily specify the molecular weights of materials, and do not have to be volatile without, however, almost forming fragment ions that serve as a reference for analyzing the chemical structure and failing to provide much chemical data.

Therefore, a more sophisticated device, i.e., a tandem MS/MS mass analyzer is used in many cases.

The GC-MS, on the other hand, uses an EI MS analyzer to obtain much spectral data owing to a high sensitivity of the EI ionization method and abundance of fragment data.

The greatest reason why the EI ionization method cannot be used in the LC is the presence of solvent; i.e., solvent ions hinder the ionization of component molecules, giving MS spectra in which CI ionization is overwhelming.

The water membrane chromatography and the gas-liquid two-phase flow chromatography offer the advantage of using the EI-ionized MS since water and solvent are present in small amounts.

Figure 3:
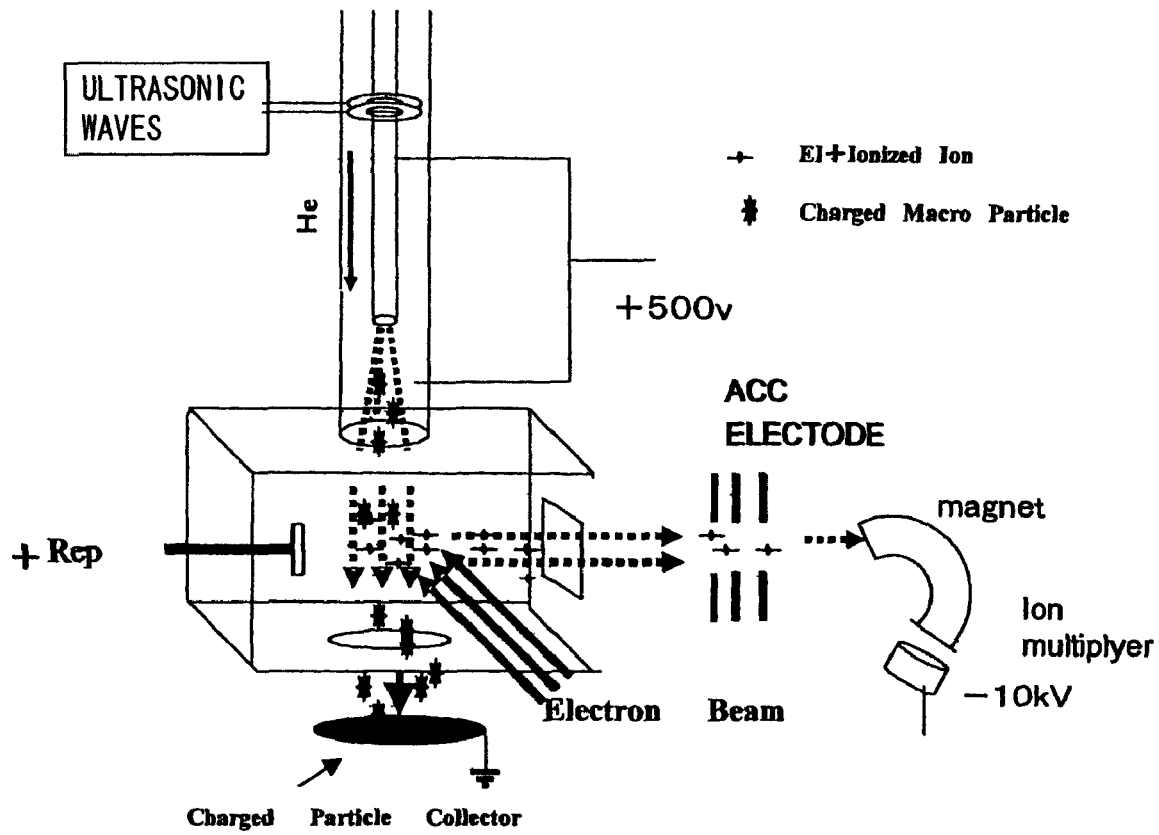
FIG. 3 is a diagram illustrating the structure of an ion source in an EI-MS apparatus as a detector portion in the analyzer of the present invention.

FIG. 3 illustrates an ion source in which a voltage equal to the potential of an ion source block is applied to the dry space of the effluent and to the particles in an ordinary EI ion source to decrease the deficit of particles that deposit on the walls and to dispose the ion source of macro mist.

The gas-liquid two-phase flow chromatography is close to the GC analyzing method from the standpoint of a medium, and it is obvious that a hydrogen flame ionization detector (FID) can be basically used by adding a makeup gas thereto.

When the apparatus of the invention is in operation, diaphragms of solvent such as water are formed maintaining a nearly regular interval in the lengthwise direction of the column in a particular gas-liquid two-phase flow state in the separator column, i.e., as schematically shown in FIG. 3, and the two-phase flow state is formed in the column moving toward the outlet of the column in a state where the gas phase and the liquid phase are intermittently alternating.

In the apparatus of the invention, to realize the above particular gas-liquid two-phase flow state maintaining stability in the separation column, the factors related to each other are suitably adjusted by taking into consideration the factors such as a flow path structure at a position where the carrier gas flow and the solvent flow meet together, properties like molecular cohesive energy (surface tension) of the solvent that is used and vapor pressure, diameter of the separation column, surface properties like solubility parameter of the solid phase material in the column, flow rates and flow ratio of the carrier gas and the solvent, speed of the mobile phase moving in the column being linked thereto, frictional force and the like.

Among them, the flow path structure at a position where the carrier gas flow and the solvent flow meet together is determined at the time of designing and manufacturing the apparatus. The flow rates and the flow ratio of the carrier gas and the solvent, as well as the moving speed in the column, are adjusted at the time of operating the apparatus. Other factors are selected and set in advance prior to operating the apparatus.

The apparatus of the invention employs means for forming a sequence of regular and intermittent water masses, i.e., employs a flow path structure in which the two mobile phases meet together. That is, when the solvent is to be fed from a pump for feeding the liquid in very small amounts, the solvent is introduced into a very thin T-shaped flow path to form a sequence of arbitrarily intermittent and regular water masses by varying the ratio of flow rates of the liquid for closing the carrier gas flow through a very fine tube and of the carrier gas (see FIG. 5).

The capillary column for analysis is connected to the outlet of the thin tube.

Figure 5A:
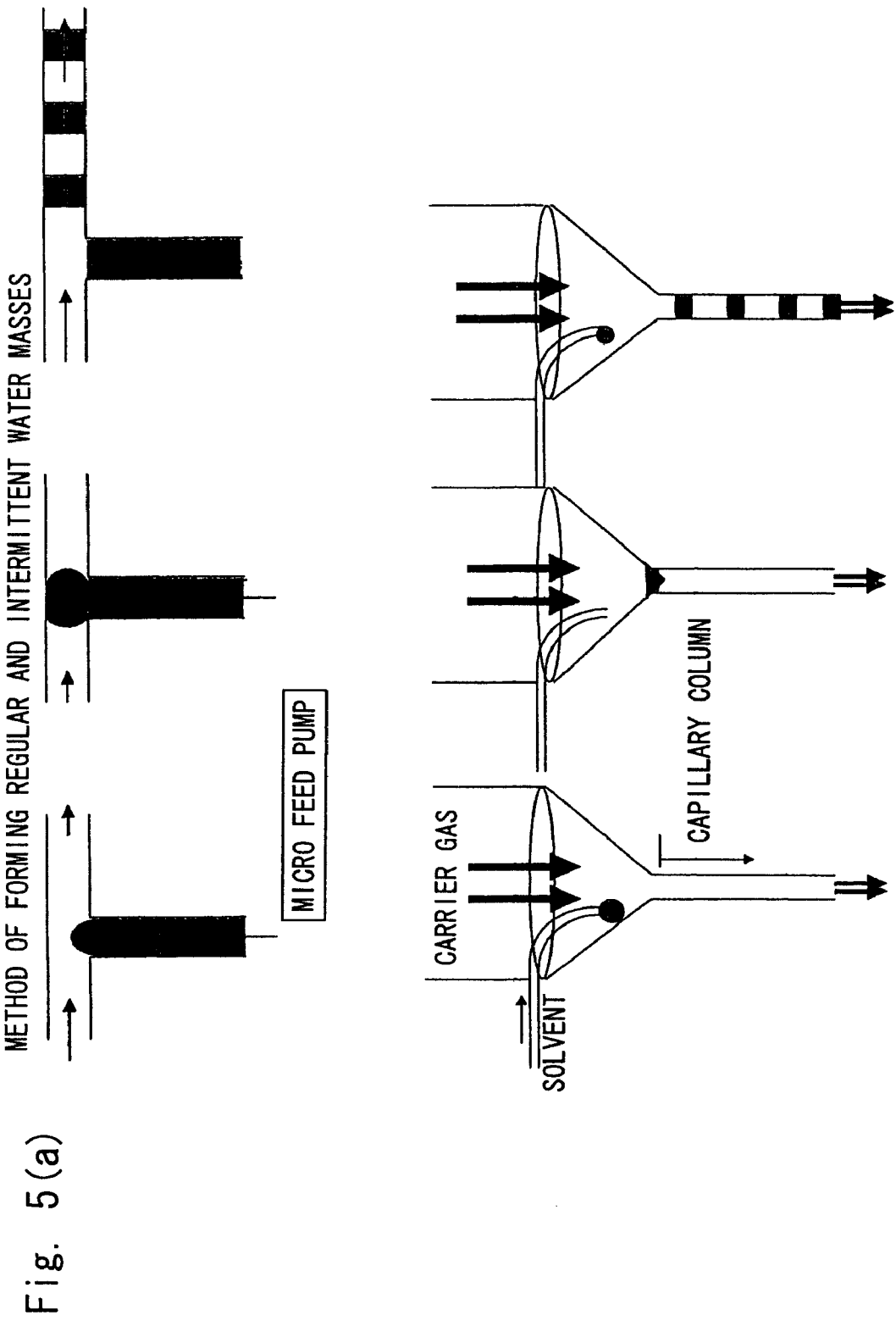
FIG. 5 is a diagram illustrating means used for forming the gas-liquid phase alternating two-phase flow state in the apparatus of the invention, wherein (a) illustrates an embodiment of directly introducing the liquid and (b) illustrates an embodiment of condensing the vapor.
Figure 5B:
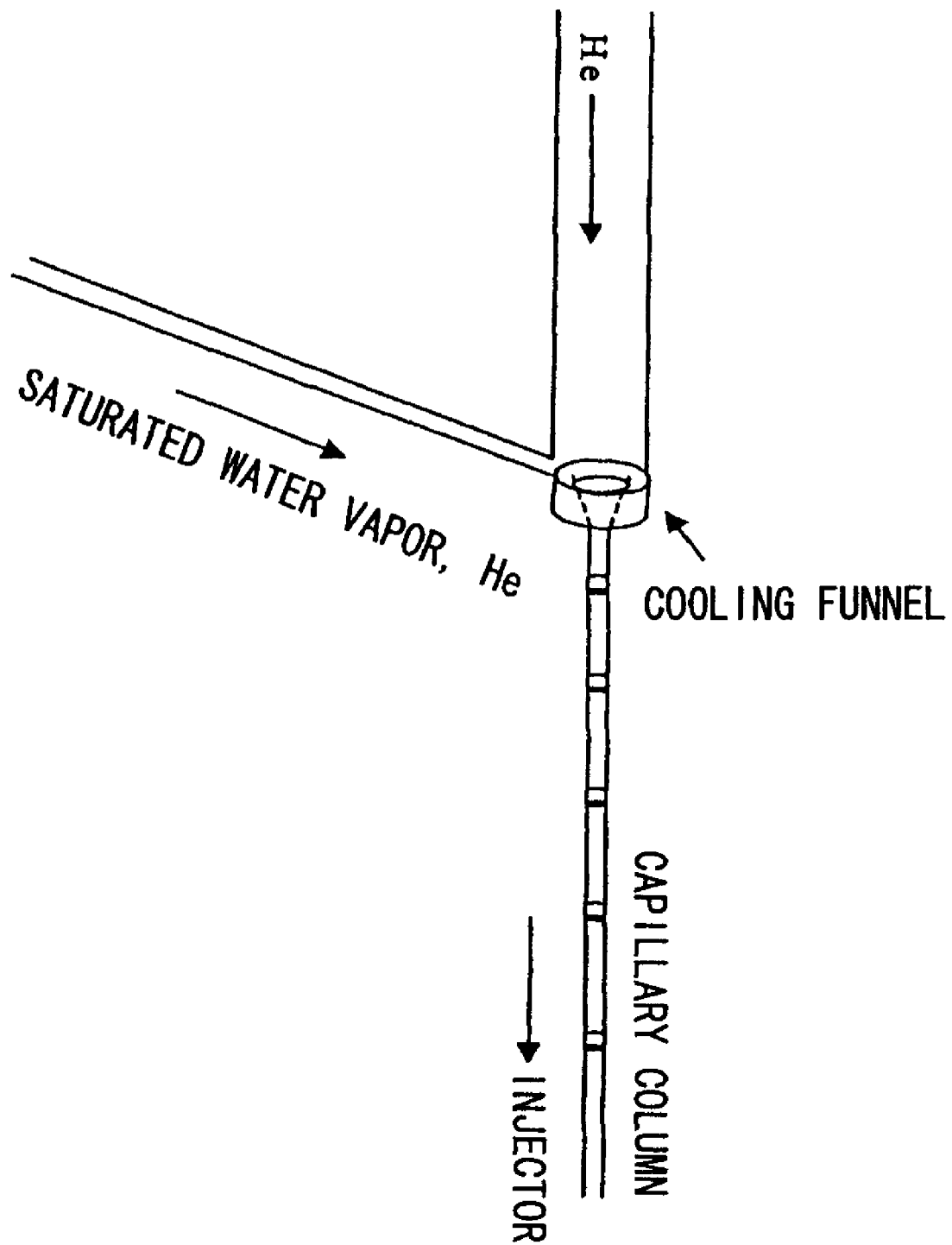

In particular, when a mixed solvent is used as the gas-liquid two-phase flow chromatography mobile phase solvent, it is desired to employ a system of FIG. 5($a$) which does not require the vaporization.

When the solvent is introduced without using the pump for feeding the liquid in very small amounts as in the apparatus of FIG. 1, the solvent vapor (e.g., water vapor from the bubbling tank in FIG. 1) is introduced together with part of the carrier gas, condensed at the inlet of the capillary column, and the condensed water masses are efficiently collected near the inlet of the column to form the closed state.

Due to the carrier gas, the manometric water masses flow into the capillary column to form a sequence of regular and intermittent water masses.

The size of water masses (plugs) can be adjusted relying upon the speed of introducing both the carrier gas and the solvent and the diameter of the tube of a portion to be closed.

FIG. 5($b$) illustrates the structure of an intermittent water mass forming unit that can be favorably used for a system based on the solvent (water) vapor condensation.

The method of forming a sequence of regular and intermittent water masses is based on the repetition of formation of the manometric state and the motion of the manometric water masses by the carrier gas.

It is desired that the surfaces of the inner walls of the device are formed by using a polytetrafluoroethylene resin having a low surface tension or is coated with a fluorine-contained surface treating agent having a perfluoroalkyl group.

A silicon-type water repellent is used for treating the surfaces to be water repellent or is used as an active group-blocking agent, and is also effective in treating the inner walls of the device used for forming the sequence of regular and intermittent water masses.

Next, described below are the flow rates and flow ratio of the carrier gas and the solvent of when structure of the apparatus, the solvent and the separation column are properly set.

That is, in the apparatus of the invention, the ratio of flow rates of the carrier gas and the solvent is so set that an average thickness of the solvent phase liquid membrane in the capillary column lies in a range of 0.1 to 1.0 μm with an average value (μm) of the estimated liquid membrane thickness in a unit time (unit: shorter than 10 seconds) as an index.

Here, the average value (μm) of the estimated liquid membrane thickness in a unit time is a value (void fraction) calculated according to the following formula (1), $$\text{Average value (μm) of the estimated liquid membrane thickness in a unit time} = \text{inner diameter of column (mm)} \times (1-\alpha) \times 10^3 \quad (1)$$

wherein α is a ratio expressed by (flow rate of gaseous volume/flow rate of the volume of the whole fluid) of the fluid in the capillary column under the atmospheric pressure.

The estimated liquid membrane thickness is an average twice value of the total thickness of the water layer on a column diameter line in a state of being condensed in the column, is determined by the inner diameter of the column and the ratio of feeding the liquid and gas media, and is a proper index for representing the state in the column.

The void fraction used in the engineering is a value which is also called percentage of void fraction, but is not suited for recognizing the state of the fluid since the value varies depending upon the inner diameter of the tube.

As a value for more generally representing the state of phase, therefore, there is defined an average value of the estimable water membrane thickness in a unit time (1 unit: shorter than 10 seconds).

The ratio of the flow rate of the liquid volume/flow rate of the gaseous volume fed into the column is determined by the amount of water (water vapor) that is fed and the flow rate of the carrier gas that is fed, and serves as the most important control index in the gas-liquid two-phase flow chromatographic separation of the present invention.

In the apparatus of the present invention, the above particular flow phenomenon in the separation column appears in a practicable range as a continuation of behavior in a unit time of shorter than 10 seconds. Therefore, abnormal intermittent water masses such as one mass in 10 meters is not included in the scope of the present invention though the closing ratio may happen to be the same.

This means that the practicable range is the one in which the interval between the two pulses detected by the mass analyzer corresponding to the gas portion sandwiched between the closing liquid plugs is not longer than 10 seconds as detected at the outlet of the column.

The average thickness of the solvent (water) membrane formed on the surface of the solid phase in a unit time (unit: shorter than 10 seconds) is a parameter capable of arbitrarily varying the flow state of the liquid membrane. Upon varying and adjusting a relationship between the amount of feeding the solvent (water) and the flow rate of the carrier gas with the above parameter as an index, it is allowed to form the solvent (water) membrane of any flow state as shown, for example, in FIGS. 6 and 7.

Figure 6:
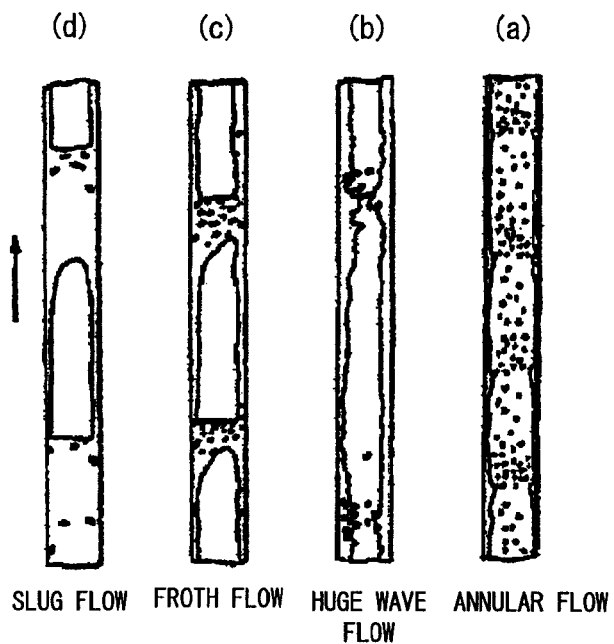
FIG. 6 is a diagram classifying the flow patterns of gas-liquid two-phase flow in a tube specified by the Japanese Association of Machinery.
Figure 7:
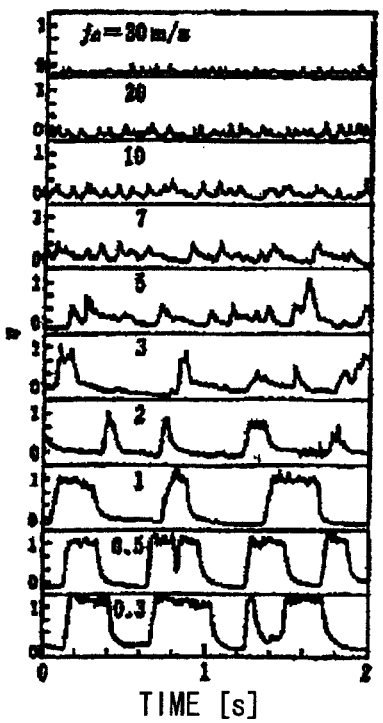
FIG. 7 is a diagram illustrating the names of flows of the gas-liquid two-phase flow in the pipe, and relationships between the air percentage and the void fraction

Incidentally, in FIG. 6, the water membrane flow states in the capillaries shown in (a), (b), (c) and (d) represent an annular flow (a), a huge wave flow (b), a froth flow (c) and a slug flow (d) in the "flowing phenomena of gas-liquid two-phase flow" specified by the Japanese Association of Machinery.

If the average value of the estimable water membrane thickness in a unit time calculated as described above is in a range of 0.1 to 1.0 μm, the mobile phase flow state in the separation column forms the particular gas-liquid two-phase flow state as intended by the chromatographic analysis of the invention, i.e., forms water diaphragms at nearly regular intervals in the lengthwise direction of the column unless other factors lie outside the proper ranges, making it possible to realize at all times the two-phase flow state in the column moving toward the outlet of the column in a state where the gas phase and the liquid phase are intermittently alternating.

More concretely, in the column of a diameter of 0.25 mm, the formed water layer (estimable water membrane thickness) becomes 250 nm and, therefore, the volume of the whole condensed water on the inner wall of the column per a length of 1 mm becomes, $$3.14 \times 0.25 \times 1 \times 0.00025 (mm) = 196 \times 10^{-6} (\mu L) = 196 \text{ pL} (0.2 \text{ nL}, 0.2 \text{ μg})/mm$$

Figure 8:
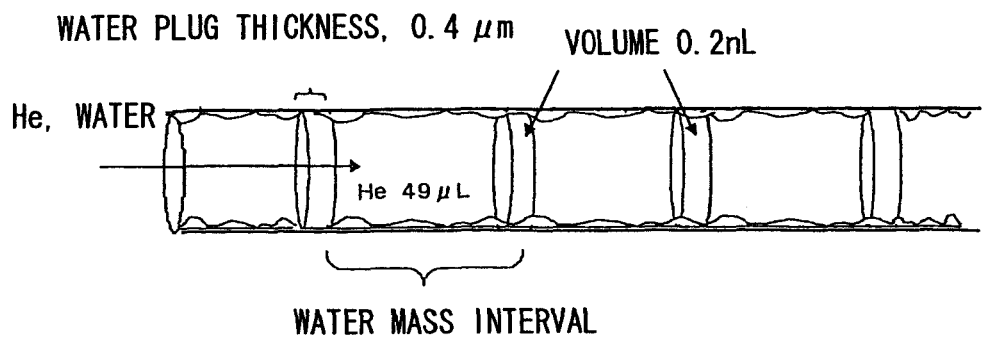
FIG. 8 is a schematic view semi-quantitatively illustrating a qualitative relationship of the gas-liquid phase alternating two-phase flow state formed in the separation column of a diameter of 0.25 mm.

FIG. 8 illustrates a case where water of an amount of 0.2 mL is allotted to the condensed water masses in the form of flat plugs as shown in a schematic diagram of FIG. 1 being arranged maintaining an interval of 1 mm.

In the column of an inner diameter of 0.25 mm, the void volume of carrier gas held in a gap between the water mass and another water mass becomes a bubble of 49 nL under the atmospheric pressure.

The column has a sectional area of 0.05 mm$^2$ and, therefore, the plug water membrane (water plug membrane) has a thickness of $400 \times 10^{-6}$ mm (=0.4 μm, 400 nm).

The liquid solvent such as water supplied to the apparatus of the invention is determined depending upon the amount of feeding the carrier gas and other requirements, and is not necessarily limited as described below. By taking into consideration the column size in the apparatus of the invention, feeding precision of the liquid feed pump and precision of bubbling amount of when the water vapor is fed, however, it is desired that an average liquid flow rate is 0.01 to 2 μL/min. and, more preferably, about 0.1 to 1.0 μL/min. from the standpoint of easily forming the flow state in the column.

Next, the second mobile phase medium used for the apparatus of the invention must be capable of easily realizing the above particular gas-liquid two-phase flow state maintaining good reproducibility. Therefore, there are selected not only a sample developer medium but also the one having limited liquid properties by taking into consideration a relation to various properties such as surface properties of the solid phase material in the separator column, molecular cohesive energy (surface tension) of the solvent, vapor pressure and viscosity.

In the above particular gas-liquid two-phase flow state of the invention, factors which are most related to the formation and stability of the manometric liquid membrane (water plug mass) are the surface tension of the solvent, vapor pressure and solubility parameter in the surface portion of the solid phase material.

The surface tension maintains the contact angle between the solvent membrane and the surface of the solid phase in the capillary column. If the contact angle becomes very smaller than 90°, the tension works in a direction for wetting the surface of the solid phase, and the membrane breaks.

Figure 4:
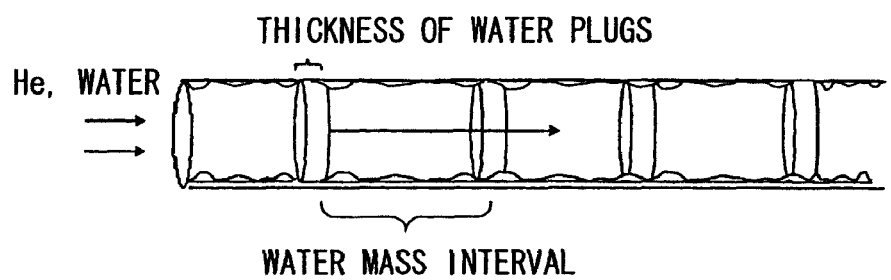
FIG. 4 is a diagram schematically illustrating a state of gas-liquid phase alternating two-phase flow formed in the separation column in the apparatus of the invention.

As for the vapor pressure, a vaporization equilibrium is maintained between the space and the membrane in FIG. 4 or FIG. 8, and a solvent vapor pressure is present corresponding to the environmental temperature.

In the drawings, the liquid membrane becomes thin as the space is filled with the saturated vapor pressure, and may often be broken.

FIG. 8 is intended to establish a gas-liquid two-phase flow state having a relatively high liquid membrane density.

When the solvent is water, the space of 49 nL contains water of a vapor pressure of 3000 Pa at 30° C., i.e., contain 1.16 pL of water. Water of this amount at 30° C. is negligible from the water membrane volume of 0.2 nL.

When the temperature is elevated or the liquid membrane interval is long, however, the amount of vaporization increases and becomes no longer negligible often causing the membrane to be broken. Therefore, it becomes necessary to suppress the amount of vaporization from the liquid membrane itself by mixing the vapor of liquid medium to the gas medium.

When the solvent is, for example, water in the gas-liquid two-phase flow chromatography of the invention, it is desired to use a solid phase resin having a water contact angle of not less than 77°.

As physical factors that are chiefly related here, there can be exemplified surface tension ($\gamma$), solubility parameter (square root of cohesive energy density; $\delta$-value), contact angle (wetting/repelling; $\theta$), etc.

When the liquid solvent which is the second mobile phase is water, it is desired that the solid phase material formed on the inner peripheral wall of the capillary column in the apparatus of the present invention is a resin or a resin composition having a contact angle with water of not smaller than 77° The resin or the resin composition may be those having a solubility parameter value (SP-value or $\delta$-value) of not larger than 18.3 $MPa^{1/2}$.

Further, the solid phase polymer may have its surfaces treated, and the treated surfaces may have a solubility parameter value of not larger than 18.3 $MPa^{1/2}$.

Concrete examples of the resin include polystyrene, polyethylene, polypropylene, polyisobutylene, vinylidene fluoride, dimethylsilicone, PTFE (polytetrafluoroethylene), and pentadecafluoroacrylate, and compositions thereof.

As a preferred resin or a resin composition, there can be used a dimethylpolysiloxane resin which is most generally used as a solid phase resin, and a polyisobutylene having water repellency that stems from a perfluoroalkyl group and, particularly, polystyrene and a branched methyl group that are contained therein in high units, and from which a wide range of use can be expected by using the radically crosslinked resin-coated membrane as the solid phase. There can be exemplified a methylpolysiloxane copolymer resin containing a fluoroalkyl group-induced siloxane monomer unit; a phenyl group-containing methylpolysiloxane copolymer resin containing a phenyl group; a resin composition having a concentration corresponding to the phenyl group mol % obtained by mixing a plurality of phenylmethylpolysiloxane copolymer resins or by mixing one or more phenylmethylpolysiloxane copolymer resins and a methylpolysiloxane copolymer resin; a cyanoalkylphenylmethylpolysiloxane copolymer resin containing cyanoalkyl group-containing siloxane monomer units at a concentration of not more than 50 mol %; and a resin composition having a concentration corresponding to the cyanoalkyl group mol % obtained by mixing a plurality of different kinds of cyanoalkylphenylmethylpolysiloxane copolymer resins or by mixing one or more cyanoalkylphenylmethylpolysiloxane copolymer resins and a methylpolysiloxane copolymer resin.

Examples of $\delta$:

Poly[dimethylsiloxane]: $\delta$=15.2
Alkylbenzene: $\delta$=18
Propionitrile: $\delta$=22
Perfluoroalkyl: $\delta$=14.5

If limited to mixing two materials only, the $\delta$-value can be estimated by an approximation based on Small's formula*. That is, the approximation of a linear interpolation by adding up the products of the respective $\delta$ and mol percentages (X), $$\delta m = X1\delta 1 + X2\delta 2$$

*(P. A. Small, J. of Appl. Chem., 3, 71 (1953)

Further, when the liquid solvent which is the second mobile phase is a mixed solution of water and an organic solvent, an organic solvent, or a mixture of organic solvents, it is desired that the solid phase material (resin or resin composition) is such that the contact angle thereof relative to the respective solvents is not smaller than 77°. The above solid phase material is selected out of the combinations having contact angles $\theta$ of not less than 77° by calculating the contact angle $\theta$ by using a relation, $$\gamma L/\gamma S = 4\phi^2/[(\cos\theta)^2 + 1]$$

of the contact angle and the surface tensions of the solvent and the solid phase material based on the solubility parameter value (or surface tension value $\gamma$L) of each of the solvents and the surface solubility parameter value (or surface tension value $\gamma$S) of the solid phase material.

When, for example, the polytetrafluoroethylene is used as the solid phase material, there can be used DMSO (dimethyl sulfoxide) or an aqueous solution of an organic solvent as a solvent in addition to the solvent of water.

For the solid phase material modified and treated for its surfaces with perfluoroalkyl groups, there can be used DMSO, DMF (dimethylformamide), acetonitrile, and an aqueous solution thereof.

Described below is an example of estimation when a combination of the above solvent and the solid phase material is to be selected.

Figure 9:
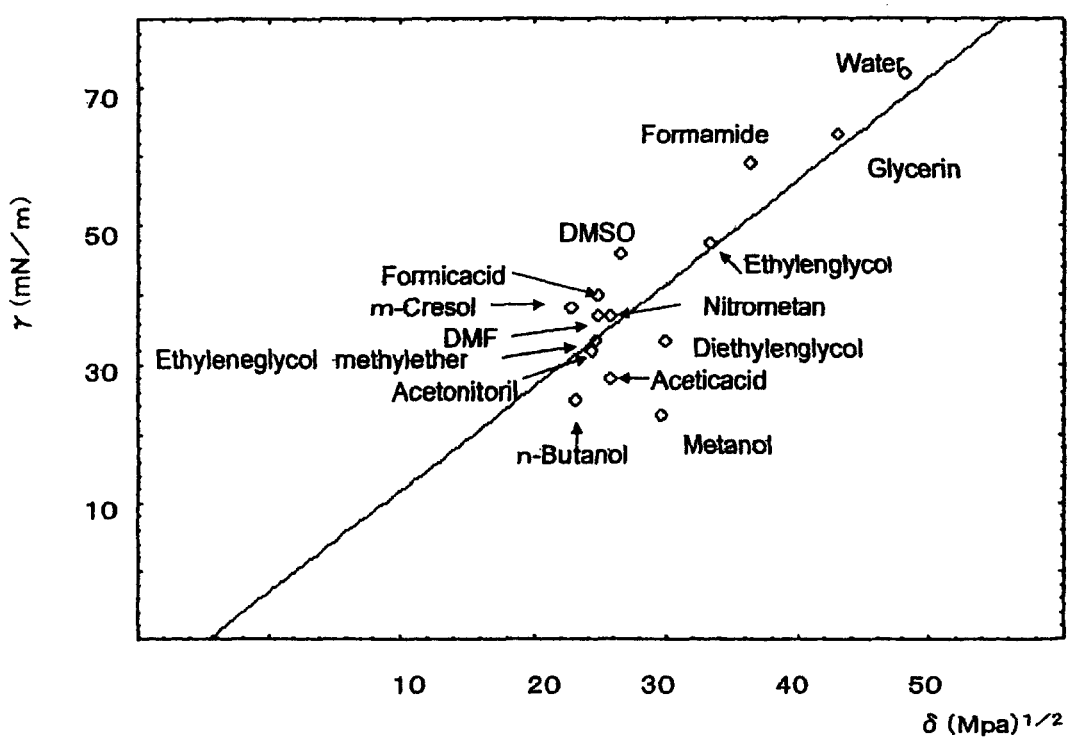
FIG. 9 is a diagram illustrating relationships between the solubility parameters of various solvents and the surface tension.
Figure 10:
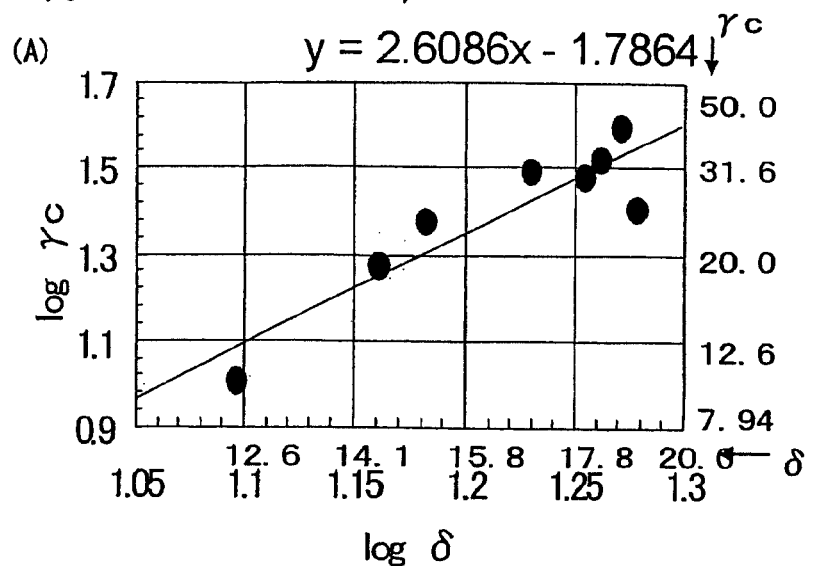
FIG. 10 is a diagram illustrating a relationship between the solubility parameter (surface tension) of a resin and the contact angle, wherein (A) is a diagram illustrating a relationship between the solubility parameter and the surface tension, and (B) is a diagram illustrating a relationship between the solubility parameter (surface tension) and the contact angle.
Figure 10:
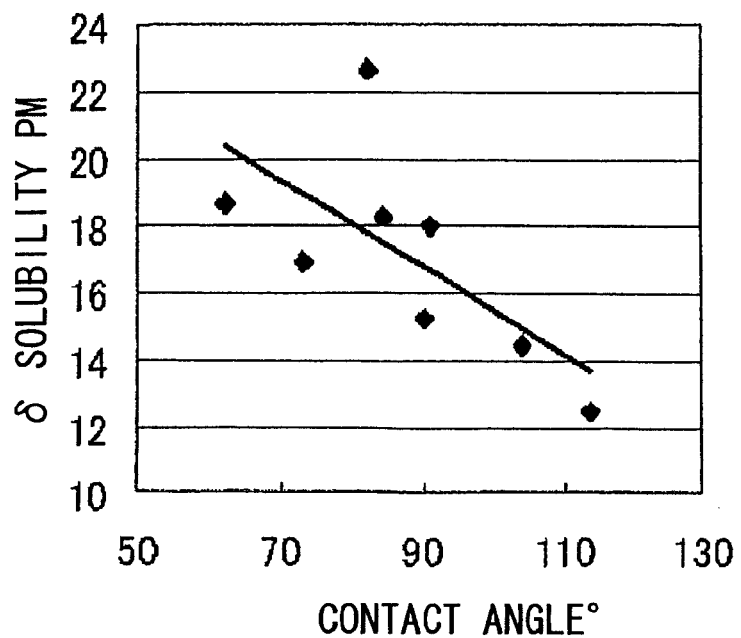

FIG. 9 is a diagram illustrating a relationship between the surface tensions ($\gamma$) of general-purpose solvents and the solubility parameters ($\delta$), and FIGS. 10(A) and 10(B) are diagrams showing correlations between the surface properties of the resin and the contact angle, from which it will be learned that only a small width of selection is obtained for maintaining the contact angle when there are used organic solvents other than water.

Further, if the solid phase can be coated with the polytetrafluoroethylene (PTFE) having the smallest surface tension and the smallest $\delta$-value as a general-purpose resin, it will be learned that the gas-liquid two-phase chromatographic conditions can be formed in combination with the polar solvent.

A fluorine alkane structure has also been formed in a modified product of silicon resin and in a silicon material introduced by using a surface-treating agent, and is considered to be useful as a solid phase.

The surface tension $\gamma$s of the resin and the surface tension $\gamma$L of the solvent have been described in the literatures related to the surface tension, like Young's formula (1805), $$\gamma s = \gamma L \cdot \cos\theta + \gamma SL$$

Wa; $\Delta$G in the adhesion work (change),
Dupure's formula; $\gamma SL = \gamma s + \gamma L - Wa$
There has been known a relationship (5) between the contact angle and the surface tension derived therefrom.

$$\gamma s = \gamma L[(\cos\theta)^2 + 1]/4\phi^2$$

$$\gamma L = 4\phi^2 \gamma s[(\cos\theta)^2 + 1] \tag{5}$$

$\gamma$s (PTFE)=18.5, cos $\theta$=0.000 (90 degrees)
$\phi$; material coefficient of solvent (0.6 to 1.1, Table 7 shows $\phi$ of a group of general-purpose solvents)

If rearranged into a $\gamma$L/$\gamma$s ratio, the relationship (5) becomes a constant, and the contact angle is determined by the properties on the solid side.

$$\gamma L/\gamma s = 4\phi^2/[(\cos\theta)^2 + 1] = 4\phi^2$$

If a polar solvent has $\phi$=1 to 1.1, water only realizes a contact angle of 90° with $\gamma$L>74.

If $\phi$=0.9 (most of the polar solvents that are usually used), $\gamma$L is 59.9.

If $\phi$=0.8, $\gamma$L is 47.4, and DMSO is included in a range.

If $\phi$=0.7, then 36.3, and DMF and AN achieve 90°, but $\phi$ are not in agreement.

If φ=0.6, then 26.6, and DMF and AN achieve 90°, but φ are not in agreement.

For the PTFE, an aqueous solution of an organic solvent can be used. In the perfluoroalkyl group surface modification treatment having smaller γs, γl=4×1×10/1 since γs=10. Therefore, there can be used dimethylsulfoxide (DMSO), dimethylformamide (DMF), acetonitril (AN) and a mixed solution thereof with water.

The water contact angle for the gas-liquid two-phase flow chromatography is estimated from a contact angle relative to the solid phase in the capillary column, and it is proper to regard it as a lower limit. The estimated contact angle is calculated as described below.

γs of the dimethylsilicone resin is 23.5. From a diagram 10(A) of γ-δ correlation, therefore, it is estimated that γs=27 in the case of a 25% phenyldimethylsilicone of δ=16.

Since γl is 72, the terms in the relationship (5) have values, i.e.,

γl/γs=2.7, the term $(\gamma L/\gamma S)^{1/2}$ is 1.64, and assuming that φ=1, then $\cos\theta = (2\phi/(\gamma L/\gamma S)^{1/2}) - 1 = 0.22$, arc cos(0.22) =77°

In the water membrane chromatography, therefore, the wet contact angle lies near 77°.

The 25% phenyldimethylsilicon resin solid phase is an upper limit of wetting/water repellency for conducting a favorable gas-liquid two-phase flow chromatography, and adjusting the amount of introducing water becomes sensitive.

A critical surface tension (γc) is an estimated value of limit surface tensions at 90° obtained by extrapolating the contact angles observed by using a plurality of solvents having different Γ. Since the contact angle of the gas-liquid two-phase flow has been discussed near 90°, there is no problem even if it is so presumed that γc≈γs.

In a range of preferred solubility parameters (δ) that can be used in the gas-liquid two-phase flow chromatography, in the case of RTX-20 of δ=15.6 which is close to the upper limit, the contact angle can be calculated from a resin δ–γc correlation of FIG. 10(A) to be, log δ=1.19, log γc=1.19×2.609−1.786=1.319

∴γc=γs=20.8, since γl=72, γl/γs=3.46, the term $(\gamma L/\gamma S)^{1/2}$ is 1.86, and assuming that φ=1, then $\cos\theta = (2\phi/(\gamma L/\gamma S)^{1/2}) - 1 = 0.0753$, Arc cos(0.0753)=86° which is considerably close to an ideal value of 90°

In the gas-liquid two-phase flow chromatography, an expansion of a range for selecting the solvent γL is expected from a combination for decreasing the lower-limit contact angle and γs.

Example of Properties:

Presuming that γs (PTFE)=18.5, cos θ=0.22 and φ=1, $$\gamma s = \gamma L[(\cos\theta)^2 + 1]/4\phi^2$$
$$\gamma L = 4\phi^2 \gamma s[(\cos\theta)^2 + 1]$$
$$= 4 \times 1^2 \times 18.5/1.488$$
$$= 49.7 \text{ (mN/m)}$$

As seen in the diagram of γ-δ correlation of solvent of FIG. 9, when a single solvent is used, the glycerin and formamide are in a region of 50 mN/m. When may of the polar solvents are used, however, they are present in a slightly lower region of 35-40 mN/m.

In this region, the surface tension can be obtained by using an aqueous solution of a polar solvent such as 10% ethanol, diethylene glycol aqueous solution or DMF aqueous solution.

In the water membrane chromatography, the distillation phenomenon takes part in the separation, and a mixed solvent is not suited. In the gas-liquid two-phase flow chromatography, however, a mixed solvent can be used, and a liquid medium of a mixed solvent type can be used if the solvent is introduced into the capillary column by a method which is not dependent upon the vaporization/condensation.

Table 1 shows properties of solvents, and Table 2 shows φ coefficients of Girifalco & Good in the water phase interface (φ is a coefficient for correcting deviation between the surface tensions of the two contacting materials and a change in the free energy of real wetting). Many compounds stay near 0.6.

TABLE 1

| Material Name | bp °C. | γ dyne/cm | δ $Mpa^{1/2}$ | Molecular vol. ml/mol | HBP |
|---|---|---|---|---|---|
| METHANOL | 64.5 | 22.55 | 29.7 | 41 | |
| DMF | 153 | 36.76 | 24.8 | 77 | 10 |
| FORMAMIDE | | 58.2/59.1 | 36.5 | 40 | |
| ACETICACID | 118 | 27.63 | 25.8 | 57 | |
| NITOROMETHANE | | 36.97 | 25.8 | 54 | 2.7 |
| DMSO | 189 | 45.8 | 26.5 | 71 | 15.5 |
| ACETONITRILE | 81.6 | 31.8 | 24.4 | 52 | 7 |
| CELLOSOLVE | 135.6 | | 23.7 | 97 | 15.5 |
| m-CRESOLE | | 38 | 22.8 | 104 | |
| n-BUTANOLE | 117.7 | 24.6 | 23.2 | 91 | |
| ETHYLENEGLYCOL | 198 | 45/50 | 33.4 | 56 | |
| GLYCERINE | 290 | 63 | 43.2 | 73 | |
| DIETHYLENGLYCOL | 244 | 33.1 | 29.9 | 95 | |
| METHYL-CELLOSOLVE | 124.6 | 33.3 | 24.7 | 79 | |
| γ-BUTYROLACTONE | | | 26.2 | 76 | |
| ETHANOLAMINE | 130.5 | | 31.7 | 60 | |
| FORMICACID | | 39.9 | 24.9 | 38 | |
| PROPYLEN-CARBONATE | 24.2 | | 27.3 | 85 | |
| WATER | 100 | 72 | 48.2 | 18 | |

HBP: Hydrogen bond parameter (square root of hydrogen bond energy density)

TABLE 2

| Material | Φ correction coefficient |
|---|---|
| Alcohols | 1.04-1.15 |
| Carboxylic acids | 0.92-1.11 |
| Carbonyls | 0.90-1.08 |
| Ester | 0.84-1.08 |
| Ether | 1.01-1.12 |
| Amine | 0.98-1.17 |
| Nitrile | 0.97-1.00 |
| Nitrated compound | 0.79-0.97 |
| Aliphatic HC | 0.53-0.60 |
| Aromatic HC | 0.61-0.73 |

Like the LC, the gas-liquid two-phase flow chromatography is conducted near room temperature, and the solid phase resin is not limited to the silicon resin-type materials that are to be used at high temperatures, but any solid phase resin can be used if it can be suitably wetted with the solvent.

Figure 11:
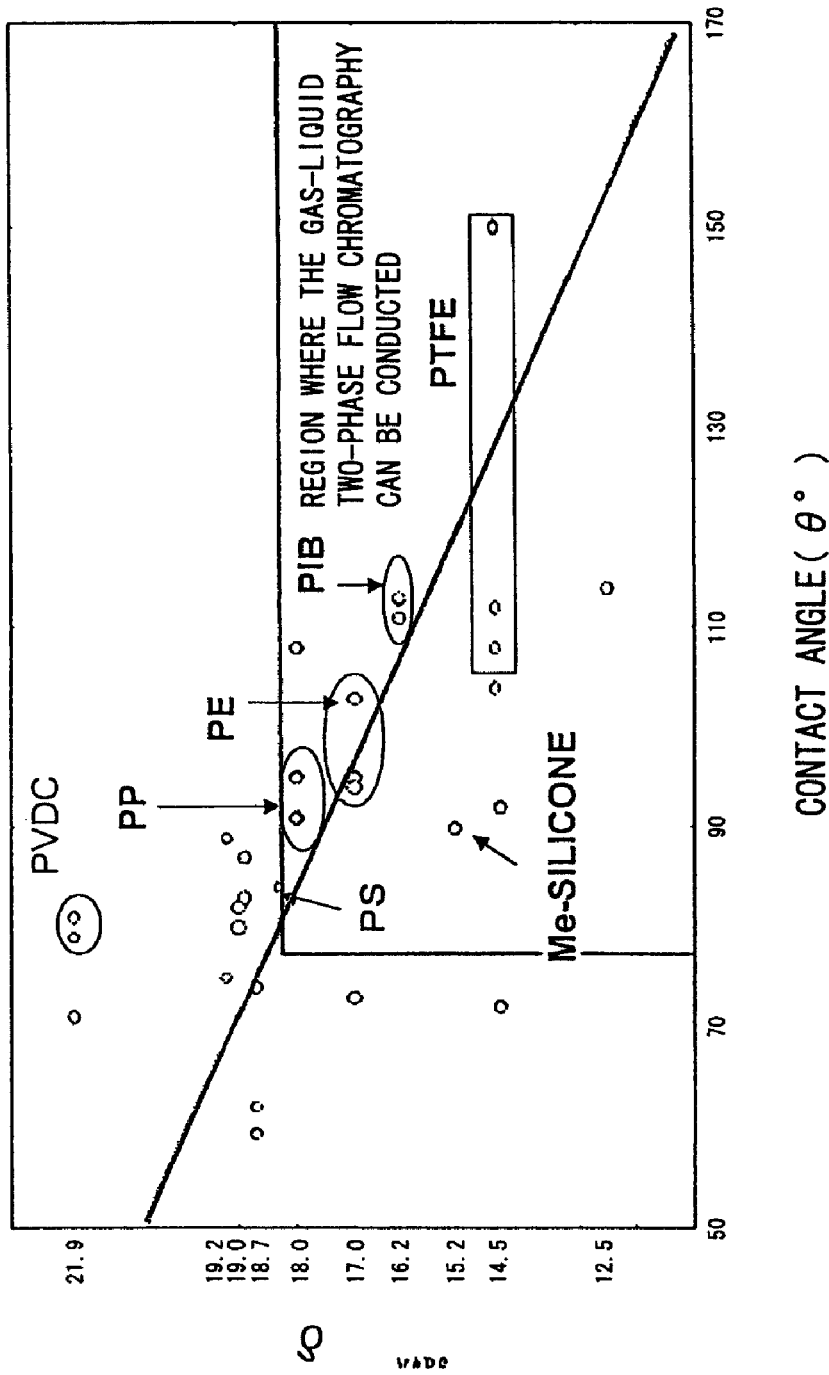
FIG. 11 is a diagram illustrating a relationship between the resins having low solubility parameter values and the water contact angles.

FIG. 11 shows the resins having small solubility parameters (δ) among the general-purpose resins in contrast with the water contact angles.

In the gas-liquid two-phase flow chromatography, it is desired that the solvent contact angle is near 90°. If this angle is too great, the contact area to the solid phase decreases, which is not desirable.

However, the materials which greatly exceed 100° are only limited materials of the perfluoroalkyl type, and are the resins that can be used since they do not forbid the formation of plug water masses.

In the drawing, the polystyrene is an upper limit of the wettable range. It is, however, considered that the crosslinked polystyrene of the crosslinked type, too, exhibits the same properties and is included therein.

The PTFE, on the other hand, is lopsided in a range of water repellency.

The PP (polypropylene), PE (polyethylene), PIB (polyisobutylene, butyl rubber) which are olefin resins can be expected to be used being applied in the capillary column so as to be turned into a three-dimensional form with a crosslinking agent if they are the resins of the noncrystalline type.

Next, it is desired that the apparatus of the present invention is provided with a mechanism for imparting sonic vibration to the capillary column.

The motion of water masses by the carrier gas pressure toward the downstream is very smaller than the water flow in an ordinary tube which is filled with water over the whole column length, but still receives the flow resistance due to friction with the tubular walls.

The water masses could be broken down if the time lengthens.

An ultrasonic motor has often been used for lowering the frictional resistance creating a desirable condition for the water masses in the capillary column to move together with the carrier gas.

It is considered that the ultrasonic vibration is desirable for assisting the motion of the water masses in the closing portions toward the downstream.

It is further considered that the ultrasonic waves contribute to mixing the component materials in the water masses.

The component molecules to be analyzed diffuse at a very slow speed in the liquid phase medium and have been known to diffuse at about 10 to 3 mm/sec. (1 μm/sec) in water.

The diffusion velocity affects the chromatography as the components diffuse in a delayed manner in the direction of thickness of water masses (in the diametrical direction of the column). The components hinder the ideally separated state in which the diffusion and mixing must have been finished before moving to the next separation site, and become a cause of losing the sharpness of separation.

The diffusion velocity in the medium liquid and the moving speed (20 to 30 mm/sec.) in the direction in which the medium flows are not balanced, and the former diffusion velocity which is too slow basically lowers the performance such as separation time and resolving power.

It is considered that the ultrasonic waves provide the stirring effect enabling a water mass to assume a homogeneous concentration.

Ultrasonic waves may have a frequency lying in a generally employed range (20 KHz to several hundred KHz) since the use of ultrasonic waves is not to effect the breakdown by vibration.

Next, described below is the analyzing method of the invention by using the above gas-liquid two-phase flow chromatographic analyzer.

The analyzing method of the invention comprises a combination of the steps of:

(A) separating and developing volatile components in a sample in a gas-solid gas chromatographic state;

(B) separating and developing polar component materials in a water membrane chromatography which forms a membrane a nearly constant but small thickness on the surface of the solid phase in the capillary column; and (C) separating and developing, in the gas-liquid two-phase flow chromatography, the component materials that are difficult to be separated and developed in the steps (A) and (B) above.

Among them, the gas-solid gas chromatography of the step (A) has heretofore been widely used for the analysis of gases and volatile components, and is not described here. Therefore, described below are the water membrane gas chromatography of the step (B) and the gas-liquid two-phase flow chromatography of the step (C) in comparison with each other.

The water membrane chromatography of the step (B) uses a chromatographic analyzer equipped with means capable of adding water or water vapor or both of them to the carrier gas, and separates and develops chiefly polar component materials by adding and mixing a predetermined amount of water, water vapor or both of them to the carrier gas so as to form a water membrane of nearly a constant thickness having an average value of estimable liquid membrane thickness in a unit time of 0.01 to 0.09 μm on the surface of the solid phase in the separation column.

On the other hand, the gas-liquid two-phase flow chromatography used in the step (C) adds a liquid solvent to the carrier gas, and permits the use of an aqueous solution of an organic solvent or an organic solvent as a liquid solvent in addition to using water.

The water membrane chromatography is essentially a gas chromatography which effects the separation and developing by distributing the gas-liquid phase based chiefly on the vaporization and condensation of water, while the gas-liquid two-phase flow chromatography is based on the liquid-solid phase distribution and is rather close to the HPLC.

Therefore, while the gas-liquid two-phase flow chromatography in many cases conducts the developing at a temperature close to normal temperature of nearly 30°, the water membrane chromatography often employs a high temperature of not lower than 100° C.

Accordingly, the column solid phase used in the water membrane chromatography employs a material which remains relatively stable even at high temperatures.

As the above solid phase, there can be used organosiloxanes such as polymethylsiloxane, polyphenylsiloxane and polyphenylmethylsiloxane; polysiloxanes obtained by chemically modifying the above organosiloxanes with a cyano group or an alkyl group; silicon grease; various polyester resins; and high molecular polyether resins.

In particular, there can be preferably used a polysiloxane polymer having a solubility parameter of 15.3 to 16.4 $MPa^{1/2}$ or a composition thereof.

The flow state in the separation column differs. The gas-liquid two-phase flow chromatography forms the froth flow (c) and the slug flow (d) in FIG. 6(a) above, while the water membrane chromatography forms the annular flow (a). The water membrane formed on the inner peripheral surface of the column solid phase has a very small thickness which is, usually, about 0.01 to about 0.1 μm and is nearly constant.

The slug flow easily forms in a fine column. Therefore, the gas-liquid two-phase flow chromatography uses a separation column having an inner diameter of, usually, 0.10 to 0.25 mm.

That is, in the gas-liquid two-phase flow chromatography, a fine column helps maintain stability of plug-like water masses (plugs) (bubbles are not easily broken), requires water in a decreased amount per a plug, and offers many advantages such as increasing the density of plugs, maintains vacuum in the MS ion source since water flows out in decreased amount per a time, and increased resolving power owing to a decrease in the diffusion region.

The water membrane chromatography and the analyzer used therefor have been disclosed in detail in JP-A-2004-333270.

The step (C) uses the apparatus described above already.

According to the method of the present invention comprising the above three steps (A), (B) and (C), the analysis may be carried out by using three apparatuses dedicated to the above steps, respectively, i.e., by using the gas-solid gas chromatographic apparatus, water membrane chromatographic apparatus and gas-liquid two-phase flow chromatographic apparatus. Or, conversely, all of these functions can be analyzed by using a single apparatus by reinforcing the function of the above gas-liquid two-phase flow chromatographic apparatus to some extent (composite chromatographic apparatus).

Or, the analysis may be carried out by using two apparatuses, i.e., the water membrane chromatographic apparatus and the gas-liquid two-phase flow chromatographic apparatus.

The composite chromatographic analyzing method of the present invention makes it possible to analyze multi-component mixed samples containing volatile materials which are gaseous at normal temperature, polar materials, sparingly volatile materials without forming azeotropic system with solvent, and polymers such as oligomers which are not substantially volatile at one time without the need of conducting any particular complex pretreatment.

EXAMPLES

Example 1

The step of separating and developing a volatile material in the GC mode based on the gas-solid distribution principle (this step is hereinafter referred to as separating/developing step (A); and the step of separating and developing a polar material in an ordinary water membrane liquid chromatographic mode based chiefly on the gas-liquid distribution principle by using a carrier gas mixed with water vapor as a mobile phase and by forming a water membrane of a constant membrane thickness on the surface of the solid phase in the capillary column by condensing the water vapor (this step is hereinafter referred to as separating/developing step (B));

were executed in the same apparatus to make sure the basic operation of a composite chromatographic mass analyzer. Namely, a chromatographic measurement was taken to develop an organic acid mixture having 1 to 9 carbon atoms as a polar material through the separating/developing step (B) only without adding, to the sample, a material that is to be developed in the GC mode.

In the separating/developing step (A), as a concentrated acetone solution containing water as little as possible, a mixture containing 1% of an organic acid was injected in an amount of 0.1 μL and was maintained at 40° C. constant for 22 minutes, and it was learned that the polar material moves difficulty if no water is contained.

Figure 12:
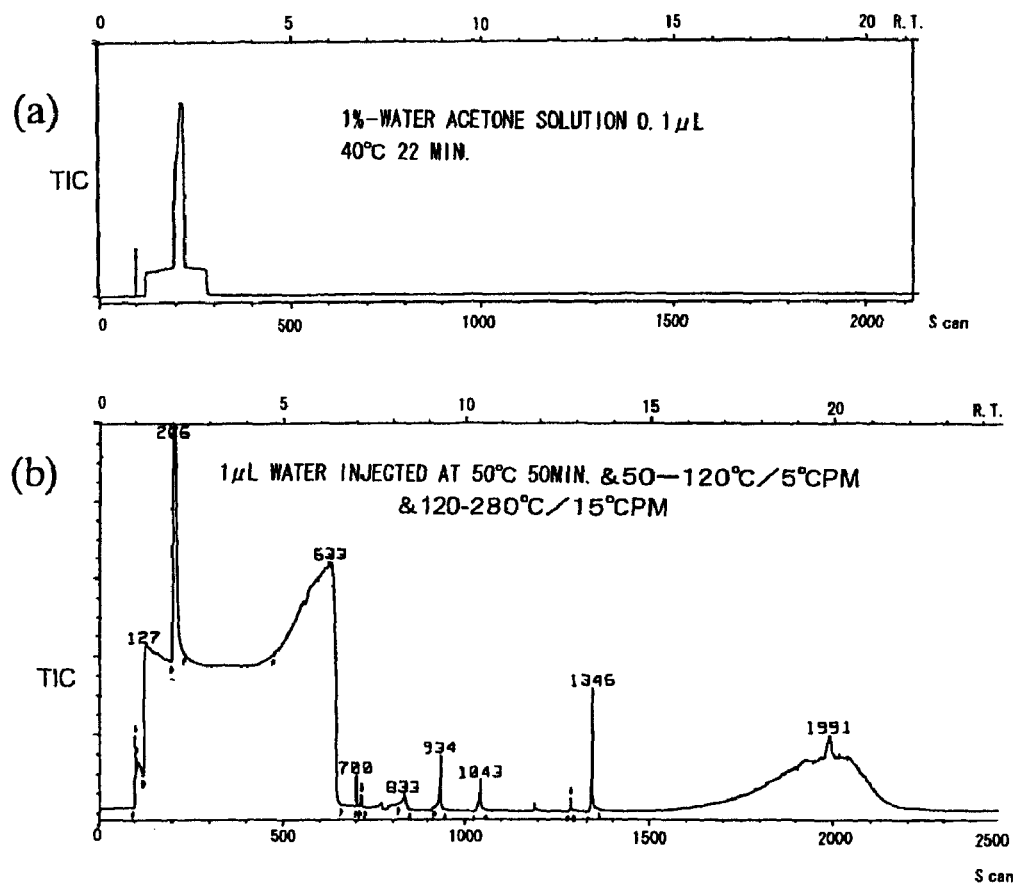
FIG. 12 is a diagram illustrating the results of analytical experiment in Example 1.

Thereafter, water only was added in an amount of 1 μL into the injection port, and the temperature was elevated at a rate of 5° C. per minute up to 120° C. and, further, at a rate of 15° C. per minute up to 280° C. while continuously feeding water at a rate of 0.4 μL per minute to thereby obtain a chart of chromatograph as shown in FIG. 12.

Capillary column: DB1701 ($\delta$=15.8 Mpa$^{1/2}$)
    0.25 mmϕ–50M Dp 1 μm,
Carrier gas: He, 330 mm/sec.
Water feed: continuously fed at a rate of 0.3 μL/min after 22 min.
Water feed rate: 0.099 mm/sec.
Houldup fraction: 0.0003
Estimable water membrane thickness: 75 nm
Temperature at injection port: 240° C.
Column: 40° C. 22 min., 50° C. 5 min.
50-120° C./5° C. per min., 120-280° C./15° C. per min.
MS apparatus: JEOL-DX303HF (field type, double convergence)
Ionization; EL+, 70 Ev, 300 μA
Measurement: SCAN mode, mass chromatographic indication GC apparatus: model HP-5890, carrier gas; He In FIG. 12, the upper stage (a) records the chromatogram of acetone and small amount of water only. In the lower stage (b), a straight-chain fatty acids of C1 to C9 are flowing out after 7.0 minutes up to 13.5 minutes.

C3 and C4 are broadened indicating that as the polarity of the component lowers, the holding time in the solid phase extends between the double distributions of solid phase resin and water.

Example 2

The separating/developing step (A) based on the gas-solid chromatographic method and the separating/developing step (B) based on the ordinary water membrane liquid chromatographic method, were executed in the same apparatus to make sure the basic operation of a composite chromatographic mass analyzer. Namely, a mineral spirit of a mineral oil-type solvent was analyzed as an example of a low boiling nonpolar material, and a hexane solution of hydroquinone (molecular weight of 110) was analyzed as a high boiling polar material.

Figure 13:
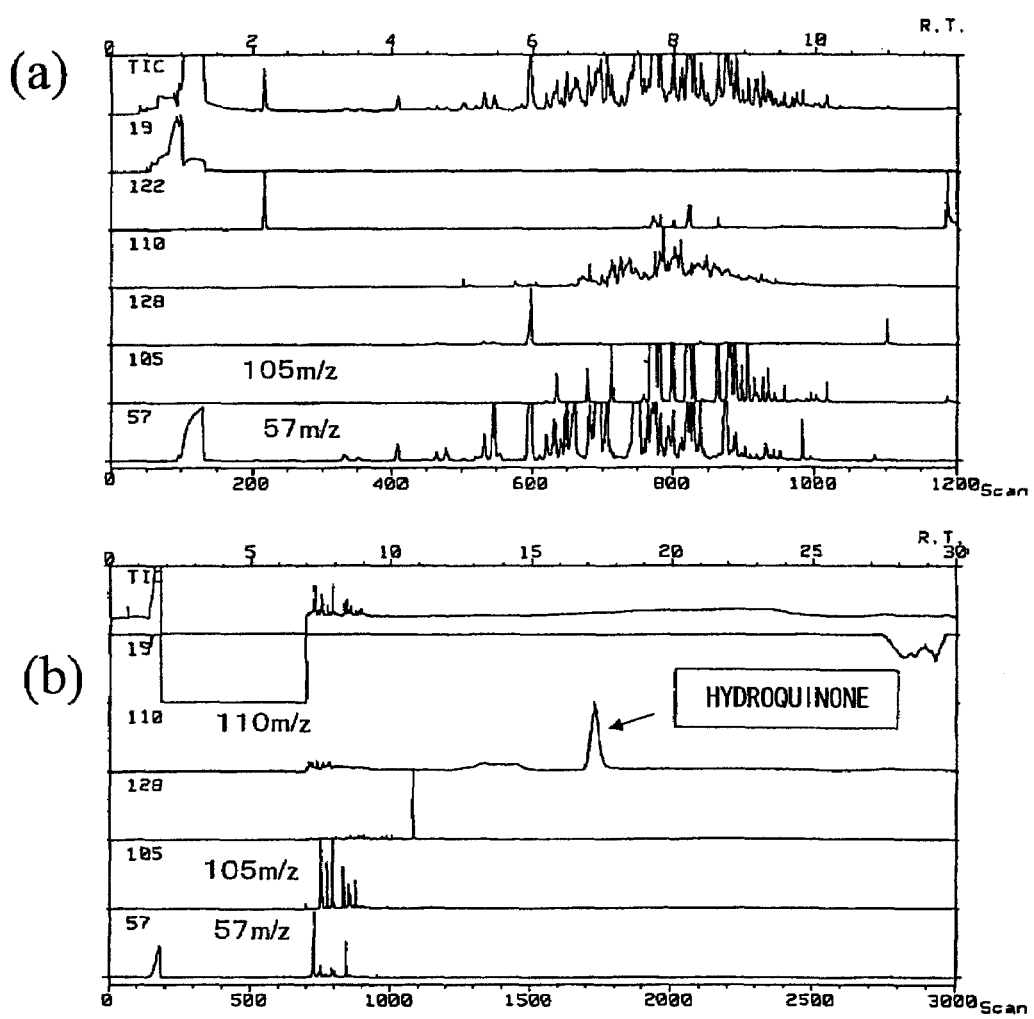
FIG. 13 is a diagram illustrating the results of analytical experiment in Example 2.

There were obtained a GCmass chromatogram (FIG. 13, upper side (a)) using the DB 1701 (14% cyanopropylphenyldimethylsiloxane polymer) in which the column solid phase possessed $\delta$ of 15.8 MPa$^{1/2}$, and a mass chromatogram (FIG. 13, lower side (b)) of a volatile material of when cooled down to 50° C. after the end of the GC mode, starting the feed of water at a rate of 0.4 μL per minute continuously, further adding 0.5 μL of water and elevating the temperature up to 280° C.

Capillary column: DB1701 ($\delta$=15.8 Mpa$^{1/2}$)
    0.25 mmϕ–50M Dp 1 μm,
Carrier gas: He, 330 mm/sec.
Water feed: continuously fed at a rate of 0.4 μL/min after 12 min.
Water feed rate: 0.136 mm/sec.
Houldup fraction: 0.0004
Estimable water membrane thickness: 100 nm
Temperature at injection port: 280° C.
Column: 50° C. (3 min)-200° C./10° C. per min.
Cooling: 50-280° C./15° C. per min.
GC-MS apparatus: same as the one used in Example 1

The mass chromatograph of the upper stage (a) of FIG. 13 is developing chiefly with a hydrocarbon index of 57 m/z ions and aromatic 105 m/z ions. In the mass chromatogram of the lower stage (b) of FIG. 13, the hydroquinone of 110 m/z only is flowing out forming a symmetrical peak near 17 minutes.

This symmetry proves the developing in the water membrane.

At the start of introducing water, part of the mineral spirit components is detected in a low-temperature region, which is derived from a polar material that is contained in a small amount.

Example 3

The separating/developing step (B) was executed first in the ordinary water membrane liquid chromatography mode, and the separating/developing step (A) was executed next in the gas-solid gas chromatography mode to make sure the operation of a composite chromatography. Namely, a polyhydric alcohol mixture of polar materials was analyzed, and an acetone solution of a mixture of paraffin, phthalic dicyclohexyl ester, pentachlorobiphenyl and squalene was analyzed as nonpolar to neutral high boiling materials.

By using AQUATIC (25% phenyl/methylsiloxane copolymer) as the column, the column was once removed from the sample injection port, the end of the column was directly inserted in the mixture solution, the mixture solution was carefully sucked by 10 mm by a reduced pressure suction method, the column was coupled again to the injection port, acetone was evaporated at 50° C. for 3 minutes, water was fed to the end of the column at a rate of 0.5 µL per minute, and after heated at 80° C. for 5 minutes, the temperature was elevated up to 120° C. at a rate of 5° C. per minute, so that lower glycols flew out.

Feeding of water was discontinued and after having monitored that all water flew out of the column at 50° C., the temperature was elevated up to 280° C. at a rate of 15° C. per minute.

Figure 14:
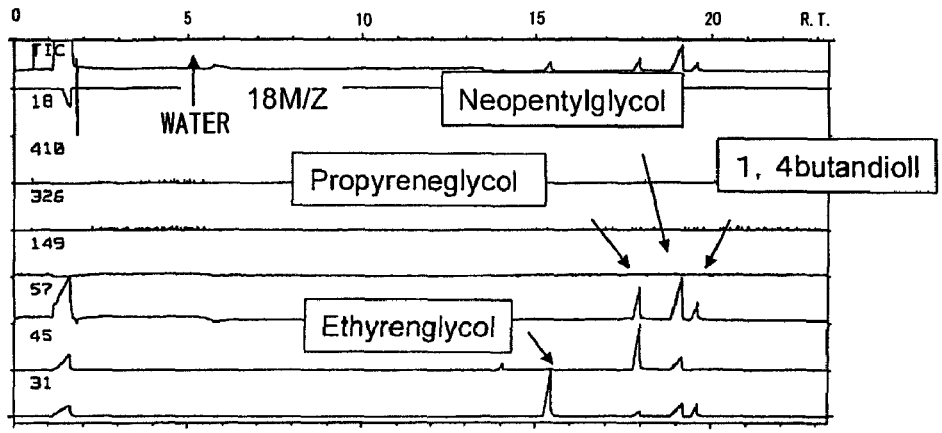
FIG. 14 is a diagram illustrating the results of analytical experiment in Example 3.
Figure 14:
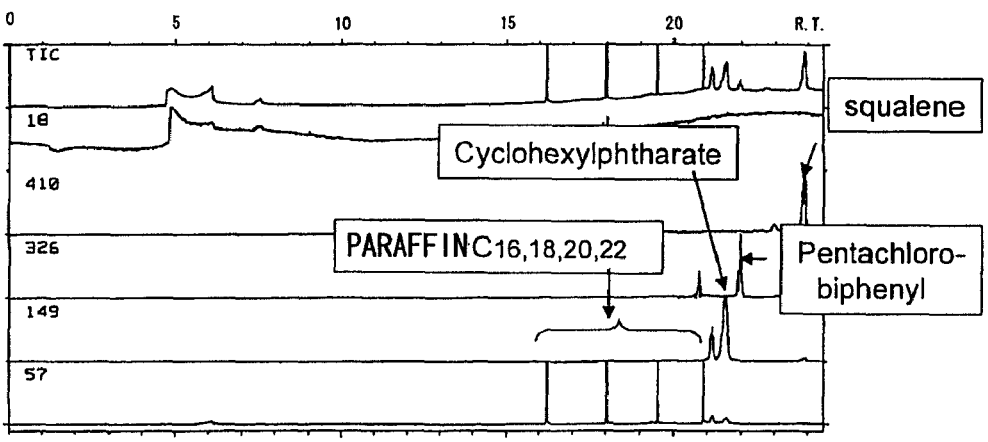

The results were as shown in FIG. 14.

The highly polar ethylene glycol, 1,3-propanediol, neopentyl glycol, and 1,4-butanediol were developed in the step of separating polar materials in the upper stage (a) in FIG. 14.

In the chromatogram in the upper stage (a) of FIG. 14, the gas flow rate was measured having substantially been increased since water vapor, too, was mixed into the carrier gas.

In the separating/developing step (A) of the lower stage, on the other hand, high boiling volatile materials such as paraffin hydrocarbons with C16, 18, 20 and 22, phthalic acid ester, pentachlorobiphenyl and squalene few out.

Capillary column: AQUATICR, 25% phenylmethylsiloxane ($\delta$=15.8 Mpa$^{1/2}$), 0.25 mm$\phi$–60M Dp 1 µm, sectional area, 0.049 mm$^2$ Carrier gas: He, 330 mm/sec.

Water feed: continuously fed at a rate of 0.5 µL/min from the first time.

Water feed rate: 0.170 mm/sec.

Houldup fraction: 0.0005

Estimable water membrane thickness: 125 nm

Temperature at injection port: 150° C.

Column: upper; 50° C. 3 min./80° C. 5 min./elevated up to 120° C. at a rate of 5° C., cooled down to 50° C. lower; after all water few out, 50 to 280° C./15° C. per minute.

GC-MS apparatus: same as the one used in Example 1

Example 4

An experiment was conducted to make sure that the separating/developing step (A) in the ordinary water membrane chromatography mode can be converted by increasing the amount of feeding water from step of developing in the gas-liquid two-phase flow chromatographic mode which features continuously forming a thin condensed water membrane on the inner wall of the capillary column, the thin water membrane not being smooth having irregularly thick portions of which a maximum membrane thickness reaching the inner diameter of the capillary column (hereinafter referred to as separating/developing step (C)).

Namely, after the step (B) of separating and developing formic acid and acetic acid by the ordinary water membrane chromatography, experiment was conducted to make sure that the motion of the medium is accelerated by the resistance produced by the contact of water membrane in the column and the flow of carrier gas when water is excessively fed by increasing the amount of water by 10 folds and by the pressure differential in the constricted portion of the tube intermittently taking place in the portions of thick water membranes.

The column DB1701 having an inner diameter of 0.1 mm$\phi$ was cut into a length of 3 meters, one side of a two-way connector of a glass capillary tube was adhered and fixed to a head portion of the column with a polyimide resin, and the other flaring opening portion thereof was installed in the GC injection port so as to face the septum.

The outlet side of the column was inserted in the MS detector through a heating interface.

The sample was injected by a method close to the on-column which inserts in the flaring opening portion by using a micro syringe through the septum.

Figure 15:
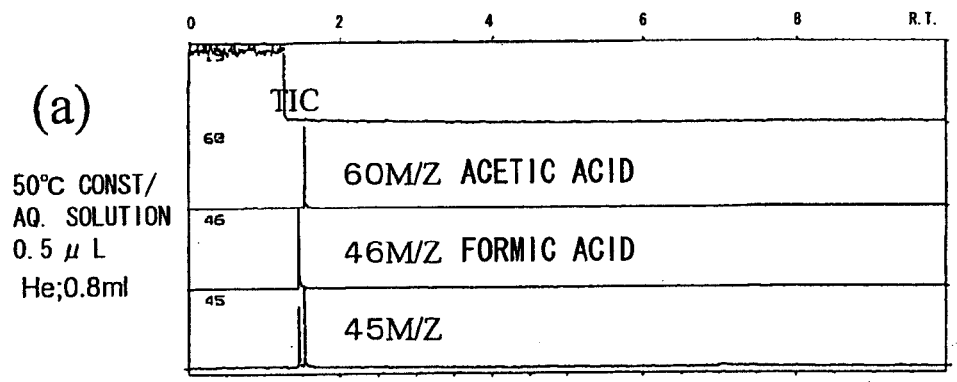
FIG. 15 is a diagram illustrating the results of analytical experiment in Example 4.
Figure 15:
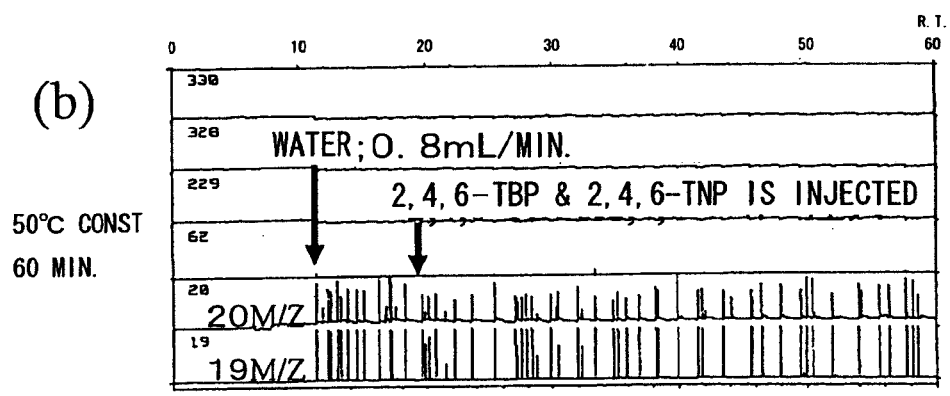
Figure 15:
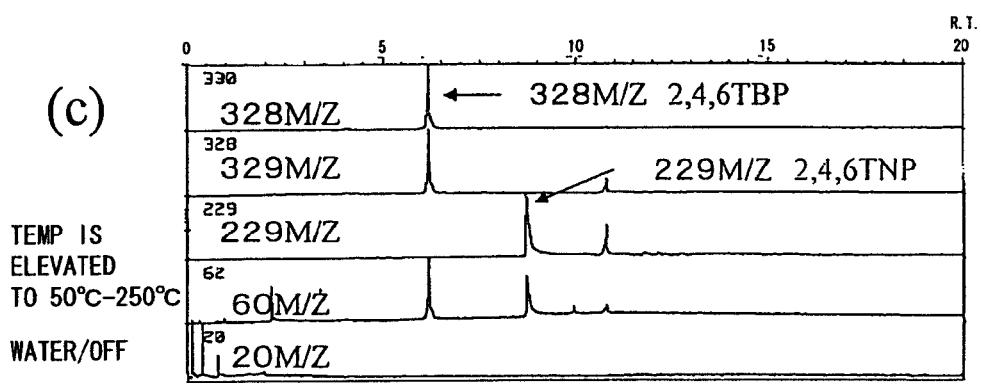

The results were as shown in FIG. 15.

First, 0.5 µL of an aqueous solution of formic acid and acetic acid was injected at an injection inlet temperature of 150° C.

In the uppermost stage (a) in FIG. 15, the GC-MS-SCAN was measured in a state of continuously feeding water at a rate of 0.08 µL per minute, and 45, 46 and 60 M/Z were shown as a mass chromatograph.

The column oven was held at 50° C. constant for 120 minutes.

Despite of a column length of 3 meters and at 50° C., the two acids were sharply separated in less than 2 minutes, and the separating/developing step (B) in the ordinary water membrane mode was achieved to a sufficient degree.

The MS measuring condition was changed into the SIM mode while the device was being held at 50° C., and the 19, 20, 62, 229 and 328 M/Z were set to the measuring channel.

Two hours after the acids were injected, the amount of feeding water was increased to 0.8 µL per minute. After stabilized for 8 minutes, 0.5 µL of an aqueous solution of a 2,4,6-trinitrophenol (TNP, Mw 229) and a 2,4,6-tribromophenol (TBP, Mw 330) was injected by the on-column injection method which was the same as the one described above.

The chromatogram of SIM mode in the intermediate stage (b) of FIG. 15 is still developing in the column since no mass signals of the two phenols are observed at 229, 328 M/Z at 50° C. in 60 minutes. On the other hand, the water ion response (19, 20 M/Z) having much spike tells that the state of water membrane formed in the column is not so flat as that in the upper stage.

Thereafter, water was no longer fed, the GC apparatus was left to stand at a constant temperature until there was no water in the column and, thereafter, the temperature was elevated up to 250° C. at a rate of 15° C. per minute.

The GC-MS interface was 280° C.

The SIM chromatograph of the lowermost stage (c) in FIG. 15 shows that the two phenols volatilized and flew out due to the heating of the column while they had been mildly separating and developing in the column in the step of separating and developing polar materials in the gas-liquid two-phase flow chromatographic mode conducted at 50° C. for 60 minutes.

From this experiment, it was made sure that the materials to be separated under the above conditions were moving together with water while enhancing the degree of separation in the column though it cannot be said that the motion is quick.

If the materials are not separating or developing in the column, the peak broadens with the passage of time due to diffusion, and the materials do not flow out sharply. Besides, the two components remain single as when injected.

It was further confirmed that upon feeding water in an increased amount, the separating/developing step (B) in the ordinary water membrane chromatographic mode could be continuously converted into the separating/developing step (C) in the gas-liquid two-phase flow chromatographic mode.

Capillary column: DB1701, ($\delta$=15.8 Mpa$^{1/2}$), 0.10 mm$\phi$–3M Dp 1 μm, sectional area, 0.0079 mm$^2$
Carrier gas: He, 340 mm/sec., 0.16 mL/min.
Water feed: 0-120 min. water is continuously fed at a rate of 0.08 μL/min. 120-180 min. water is continuously fed at a rate of 0.80 μL/min.
Water feed rate: 0.169 mm/sec., latter half; 1.69 mm/sec.
Houldup fraction: 0.00050, latter half; 0.0050
Estimable water membrane thickness: 50 nm, latter half; 500 nm
Injection: on-column injection, 150° C.
Temperature: column 50° C., 180 min. 50-250° C./elevated at a rate of 15° C. per minute.
GC-MS apparatus: same as the one used in Example 1
Measurement: SCAN mode, latter half; SIM mode Example 5

In the separating/developing step (C) in the gas-liquid two-phase flow chromatographic mode, an experiment was conducted to accelerate the motion of a thin water membrane due to the gas-liquid two-phase flow by giving ultrasonic waves thereto from the exterior of the capillary column, and the phenomenon thereof was confirmed.

A capillary column DB1701 of a diameter of 0.25 mm and 3 meters long was provided, and was so arranged as to start from a column oven and to return back to the column oven detouring an external ultrasonic bath.

The column oven was set at 150° C., the capillary column over a length of 2 meters was dipped in a hot water in the ultrasonic bath, and the outlet side of the column was returned back to the column oven and was inserted in the MS ion source through an interface heated at 250° C.

The 2,4,6-trinitrophenol (TNP) was on-column injected into the column, the medium was flown while feeding He gas at a rate of 0.2 mL/min. and water at a rate of 0.4 μL/min, and ultrasonic vibration of an output of about 30 watts and 39 KHz was imparted to the capillary column. In this case, the TNP quickly flew out even at a bath temperature of 50° C.

Figure 16:
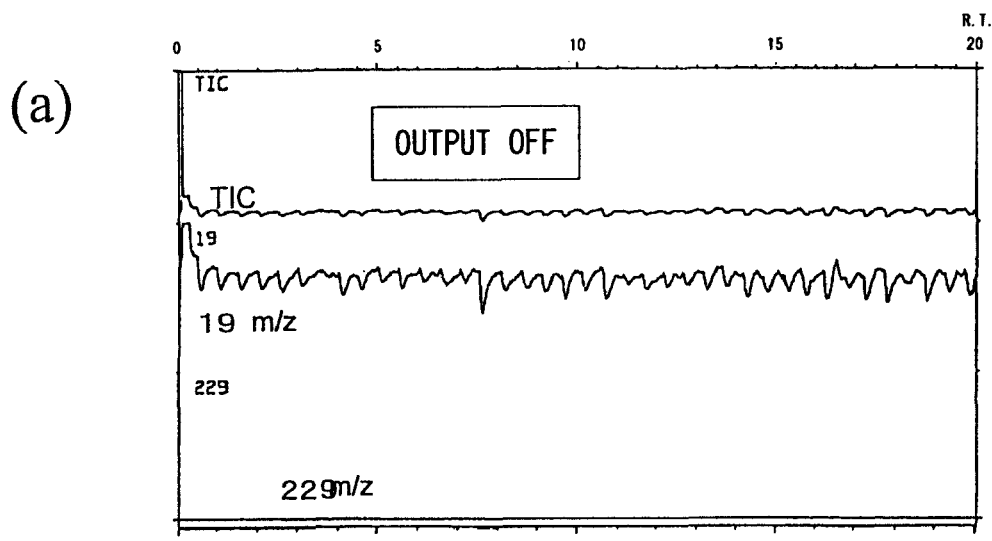
FIG. 16 is a diagram illustrating the results of analytical experiment in Example 5.
Figure 16:
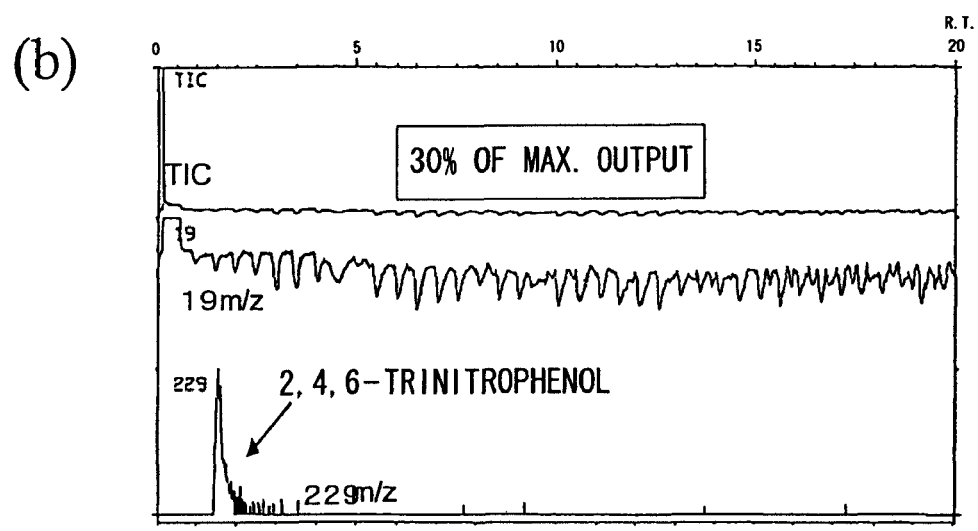

In the case of the upper stage (a) of FIG. 16 without ultrasonic waves, however, the flow out was confirmed by using the MS for the first time when the capillary column was taken out from the bath 20 minutes after the developing and when the whole column was returned back to the column oven and was heated at 150° C.

Without the ultrasonic waves, the TNP could not move to the column outlet, but could be moved upon the heating and volatilization.

In the drawing, the 19M/Z mass chromatograph shows a state where water is excessively fed into the column but is stably flowing as a slug flow as referred to by the gas-liquid two-phase flow mechanical engineering and where the flow state is not vigorously varying due to ultrasonic waves but rather the TIC signals (b) are less rugged than (a), and the slug flow is stabilized by the application of ultrasonic waves.

The fact that the TNP to be separated has moved in the column of 50° C. due to the application of ultrasonic waves is obvious from the comparison of the two data (FIGS. 16(a) and 16(b)).

Capillary column: DB1701, ($\delta$=15.8 Mpa$^{1/2}$), 0.25 mm$\phi$–3M Dp 1 μm, sectional area, 0.049 mm$^2$
Carrier gas: He, 68 mm/sec., 0.2 mL/min.
Water feed: continuously fed at a rate of 0.4 μL/min. (water is vaporized at 150° C.)
Water feed rate: 0.136 mm/sec.
Houldup fraction ($\gamma$): 0.0020
Estimable water membrane thickness: 500 nm
Injection: on-column injection, 150° C.
Temperature: column 150° C. GC-OVEN—50° C. constant temperature water tank—150° C. GC-OVEN
GC-MS apparatus: same as the one used in Example 1
Measurement: SCAN mode
Ultrasonic waves: 100 watts, 39 KHz with water tank, used at 30% output Example 6

As described in Example 5, it was confirmed that the motion of the thin water membrane by the gas-liquid two-phase flow could be accelerated by applying ultrasonic waves from the exterior of the capillary column in the separating/developing step (C) in the gas-liquid two-phase flow chromatographic mode. Thereafter, the state of separating the high boiling phenol mixture was examined under the condition of returning the capillary column DB1701 of a diameter of 0.25 mm and 3 meters long from the column oven to the column oven detouring the external ultrasonic bath.

The column oven was set at 150° C., the capillary column over a length of 2 meters was dipped in water in the ultrasonic bath of 30° C., and the outlet side of the column was returned back to the column oven and was inserted in the MS ion source through an interface heated at 250° C.

A mixed solution of the 2,4,6-trinitrophenol (TNP) and the 2,4,6-tribromophenol (TBP) was on-column injected in an amount of 0.1 μL into the column, the medium was flown while feeding He gas at a rate of 0.4 mL/min and water at a rate of 0.4 μL/min, and ultrasonic vibration of an output of about 30 watts and 39 KHz was imparted to part of the capillary column inserted in the water tank.

After maintained at a temperature of 30° C. for 40 minutes, the capillary column was taken out of the bath, the whole column was returned back to the column oven and was heated up to 290° C. to confirm the TBP and TNP by using the MS.

Figure 17:
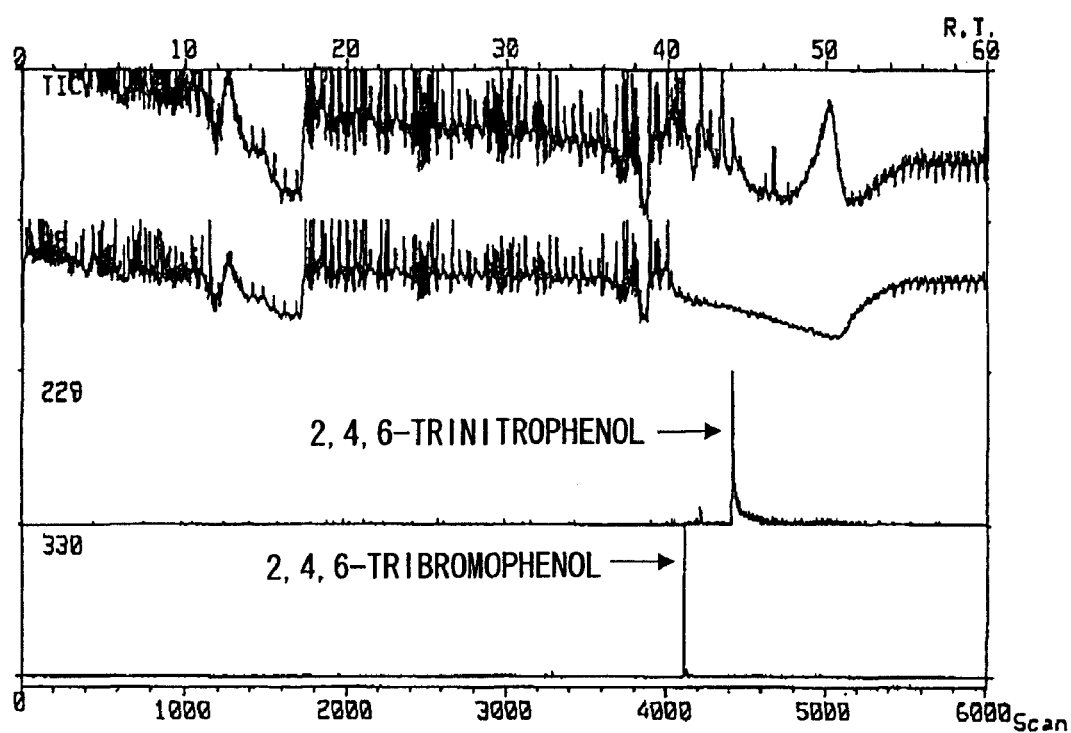
FIG. 17 is a diagram illustrating the results of analytical experiment in Example 6.

In the FIG. 17, the 19 M/Z mass chromatograph shows a state where water is excessively fed into the column and unstable flow is taking place in which the slug flow is mixed due to the annular flow and the huge wave flow.

The mass chromatograms of 330 and 229 M/Z have no trace that indicates the flow out of the two phenols due to ultrasonic waves, but show they flew out for the first time due to volatilization accompanying the rise in the column temperature.

However, the sharpness of TBP and TNP peaks are astonishing considering from the separation and development in the capillary column of a length of one meter at substantially 30° C. being dipped in the water tank, from which it can be sufficiently presumed that the liquid-solid thin membrane distribution and separation had been mildly undergoing due to the gas-liquid two-phase flow chromatography.

The apparent resolving power of the chromatogram related to the TBP exceeds several hundreds of thousands of plates.

Capillary column: DB1701, ($\delta$=15.8 Mpa$^{1/2}$), 0.25 mm$\phi$–3M Dp 1 µm, sectional area, 0.049 mm$^2$
Carrier gas: He, 1360 mm/sec, 4 mL/min.
Water: continuously fed at a rate of 0.4 µL/min. (water is vaporized at 150° C.)
Water feed rate: 0.136 mm/sec.
Houldup fraction ($\gamma$): 0.00001
Estimable water membrane thickness: 500 nm
Injection: on-column injection at room temperature.
Temperature: 1) column oven 150° C.-30° C. constant temp. water tank, 40 min.
2) column oven RT-290° C., quickly heated.
GC-MS apparatus: same as the one used in Example 1
Measurement: SCAN mode
Ultrasonic waves: 100 watts, 39 KHz with water tank, used at 30% output Example 7

Experiment was conducted to change over the lower limit and upper limit conditions for feeding water in the ordinary water membrane chromatographic mode by using a wide-bore capillary column HP624 coated with a solid phase for capillary column adapted to analyzing water quality environment and particularly for analyzing trihalomethane.

The column was cut into 7 meters long, a capillary blank tube of a diameter of 0.1 mm and a length of 40 cm treated to be inert was connected to an end of the column through a three-way connector and was inserted in the MS ion source, and a capillary blank tube of a diameter of 0.25 mm and 40 cm long treated to be inert was connected to another port of the connector, and He was divided into ½8 to reduce the He carrier gas flow rate so as to maintain the MS ion source vacuum.

Water was continuously fed at a rate of 1 µL per minute directly into an ordinary glass insert-type GC injection port maintained at 150° C. through the septum without using the water vapor reservoir.

The sample was injected through the septum by the on-column injection method of the injector-incorporated type.

The sample for the ordinary water membrane chromatography was on-column-injected in an amount of 0.2 µL onto the column HP624 of a diameter of 0.53 mm$\phi$ by using an aqueous solution containing straight-chain saturated fatty acids of from C1 to C9.

The temperature was elevated up to 150° C. while flowing the He carrier gas at a flow rate of 23 mL/min. 10 Minutes thereafter, the column was cooled down to 50° C. to end the separating/developing step.

The injection port was heated at 280° C., water was continuously introduced at a rate of 5 µL/min, and 19 M/Z ions were monitored and left to stand until the degree of vacuum and the base line varied maintaining stability.

As another sample in the ordinary water membrane chromatography mode, further, 0.1 µL of a 2,4,6-tribromophenol (TBP) aqueous solution was on-column-injected.

The He carrier gas was flown at a rate of 19 mL/min, and the column was held at a temperature of 50° C. for 40 minutes.

During this period, there was no TBP ionic response of 330 M/Z. Thereafter, the temperature was elevated up to 250° C. at a rate of 15° C. per minute to confirm the flow out of TBP.

Figure 18:
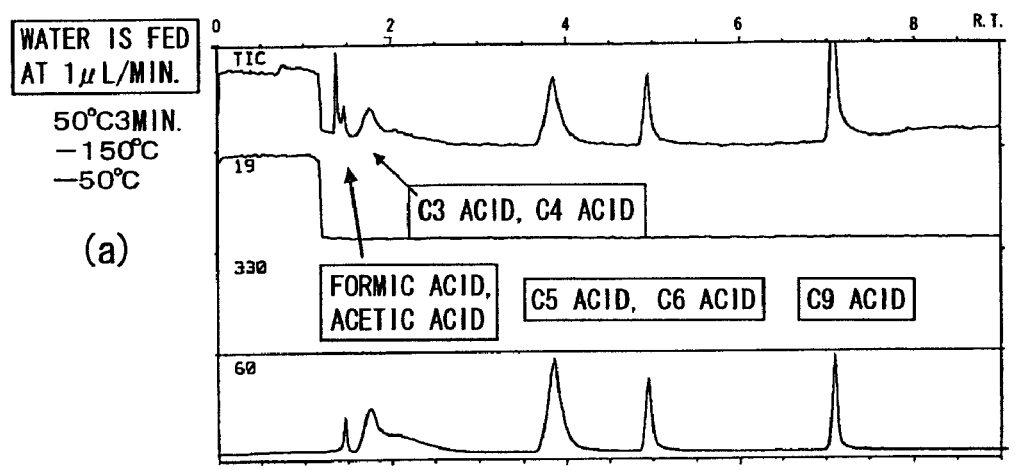
FIG. 18 is a diagram illustrating the results of analytical experiment in Example 7.
Figure 18:
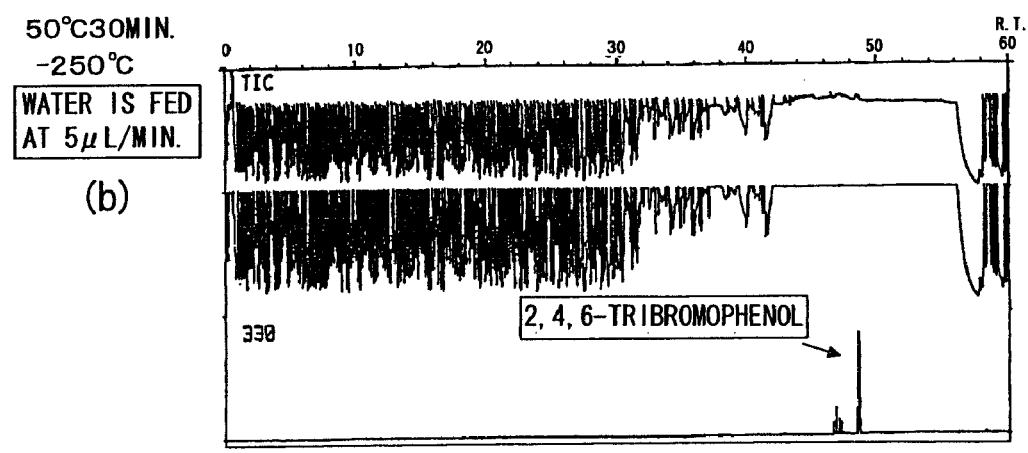

As for the amount of feeding water in the water membrane chromatography, the upper stage (a) in FIG. 18 shows an estimable water membrane thickness of 5 nm (0.005 µm). The separation state is very inferior to that of drawings of Example 1 concerning the peak width and separation capability that are seen in the chromatograms.

The effect of water membrane is seen to some extent in the symmetry of peaks, which, however, cannot be used in the step of separating and developing polar materials.

The lower stage (b) in FIG. 18 shows an estimable water membrane thickness of 30 nm (0.03 µm). In the wide-bore column, despite water is fed in an amount as large as 5 µL, an excessively fed state is not occurring, and a 19 M/Z response curve is expressed containing noise attributed to annular flow to huge wave flow.

This is because the sectional area is 4.5 times as large as that of 0.25 mm$\phi$ and the carrier flow rate is great.

However, the high boiling material to be separated does not exhibit the effect of distilling and moving the water vapor under the above column condition, and flows out for the first time when volatilized at an elevated temperature.

The separation pattern is obtained as a sharp peak which is a feature of the water membrane chromatography.

This experiment proves that the idea of the estimable water membrane thickness also applies to the water membrane chromatography of columns of different diameters.

Capillary column: HP624, ($\delta$=15.35 MPa$^{1/2}$), 0.53 mm$\phi$–7M Dp 1 µm, sectional area, 0.221 mm$^2$
[First Condition]: carrier gas; He, 7820 mm/sec, 23 mL/min.
Water feed: 0-10 min. water; continuously fed at a rate of 1.0 µL/min.
Injection port temperature: 150° C.
Water feed rate: 0.0754 mm/sec.
Houldup fraction: 0.00001
Estimable water membrane thickness: 5 nm
[Second Condition]: carrier gas; He, 6460 mm/sec, 19 mL/min.
Water feed: 0-60 min. water; continuously fed at a rate of 5 µL/min.
Injection port temperature: 280° C.
Water feed rate: 0.377 mm/sec.
Houldup fraction: 0.00006
Estimable water membrane thickness: 30 nm
Injection: on-column injection at 150° C. and 280° C.
GC-MS apparatus: same as the one used in Example 1
Measurement: SCAN mode Example 8

The chromatography of a high boiling polar material mixture in the gas-liquid two-phase flow chromatographic mode was carried out by the cartridge type on-column injection.

The capillary column AQUATICR having a diameter of 0.25 $\phi$ and 60 meters long was maintained at 55° C. constant, and the whole amount of water vapor was fed at a rate of 1 µL/min which was the lower limit of control of the liquid feed pump for the high-performance liquid chromatography.

The sample solution was an acetone solution of a lower fatty acid and a mixture of phenols, and was injected by using a cartridge in the on-column injection method.

Concretely, the sample solution was sucked into a 0.25 mm capillary column blank tube of 30 mm long by 1 cm relying on the capillary phenomenon, and was readily inserted in the opening of a glass capillary column connector.

The amount of injection was 5.0 µL.

Water was continuously fed for 34 minutes at an allowable limit of vacuum of the MS apparatus, and the high voltage of the ion source was interrupted to end the experiment.

The 19 M/Z signals at this moment maintained a steady state repeating the same protuberance and dent though the stability was poor.

However, the ion source was protecting the vacuum intermittently.

After the acetone has flew out, high boiling phenols, too, flew out in a short period of time at a column temperature of 55° C. constant.

The chromatogram was very sharp, and a resolving power of several hundreds of thousands of plates is estimated even relying on a simple calculation.

The high resolving power is probably brought about by the water membrane of a thickness of not larger than 0.1 μm that participated in the separation and a slow diffusion velocity in water of the materials to be separated.

The mass chromatograph channel of 45 M/Z shows the state of developing carboxylic acids, and 110 M/Z shows the state of developing phenols.

It is not obvious from what modified ions the 110 M/z stems.

Figure 19:
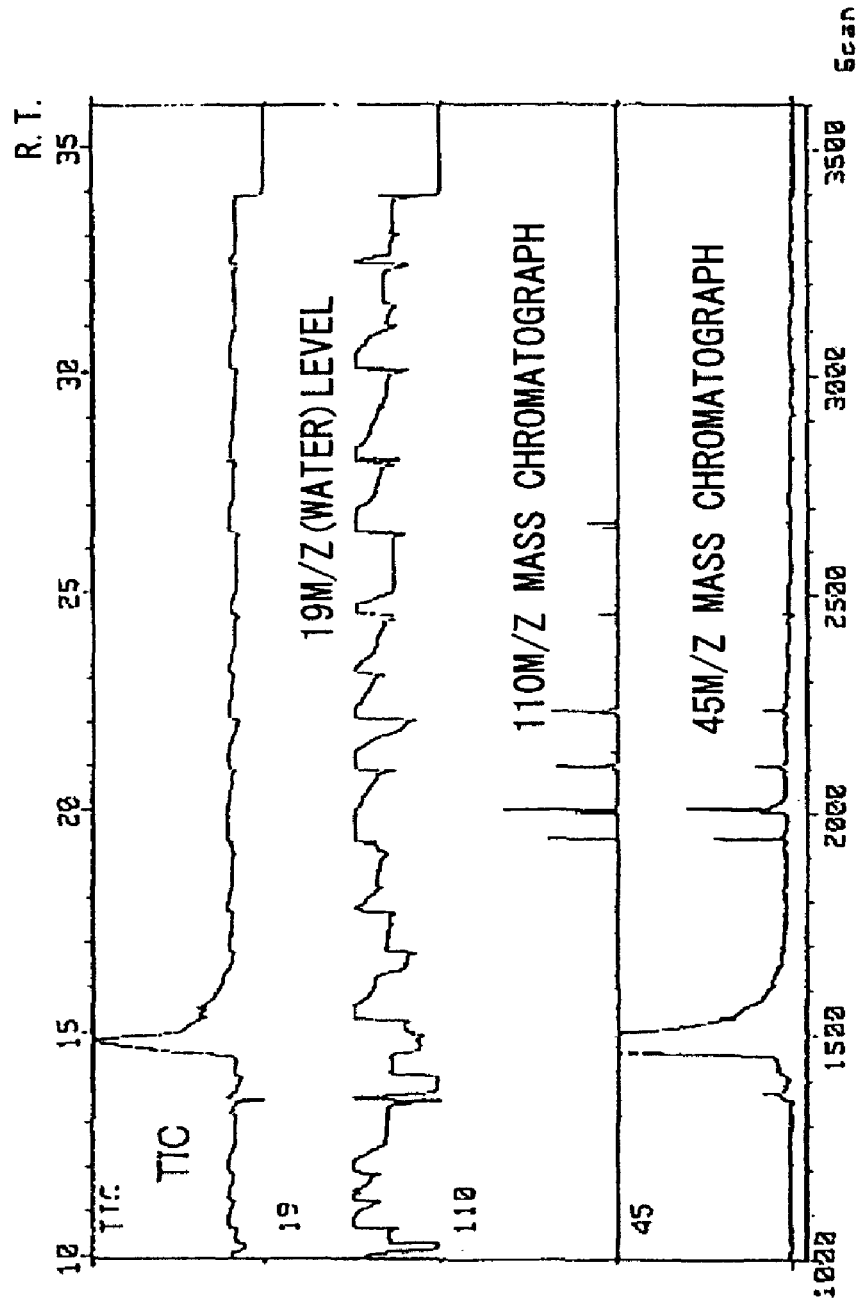
FIG. 19 is a diagram illustrating the results of analytical experiment in Example 8.

In the flow pattern of the gas-liquid two-phase flow mechanical engineering, the slug flow is apparently distinctive, and it is presumed that the chromatogram of FIG. 19 was formed as a result of smooth migration of the materials.

The interface before the ion source was 280° C., and the components were volatilized and were ionized together with the water vapor.

Capillary column: AQUATICR, 25% phenylmethylsiloxane ($\delta=15.8$ Mpa$^{1/2}$) 0.25 mmϕ–60M Dp 1 μm, sectional area, 0.049 mm$^2$ Carrier gas: He, 210 mm/sec 0.62 mL/min.

Water feed: continuously fed at a rate of 1 μL/min (vaporized at 150° C.).

Water feed rate: 0.340 mm/sec.

Houldup fraction (γ): 0.0016

Estimable water membrane thickness: 400 nm

Temperature of injection port: 150° C.

Column: 55° C. constant

Interface: 280° C.

GC-MS apparatus: same as the one used in Example 1

Measurement: SCAN mode

Example 9

The drawing shows a TIC (total ion monitor) chromatogram of a change of state of water that vaporizes at the injection port of 150° C. and condenses in the column of 40° C. edited from an EI+ ionization MS spectra of water by using helium as the carrier gas, distilled water dissolving carbonic acid gas therein as the second mobile phase medium, by varying the flow rate of the carrier gas from 2.7 mL/min. to 0.8 mL/min., and by stepwisely varying the distilled water from 0.35 μL/min. to 0.65 μL/min. The column was a dimethylsilicone capillary column having an inner diameter of 0.25 mm and 30 meters long, and the solubility parameter (δ) was 15.2 MP$^{1/2}$.

Figure 20:
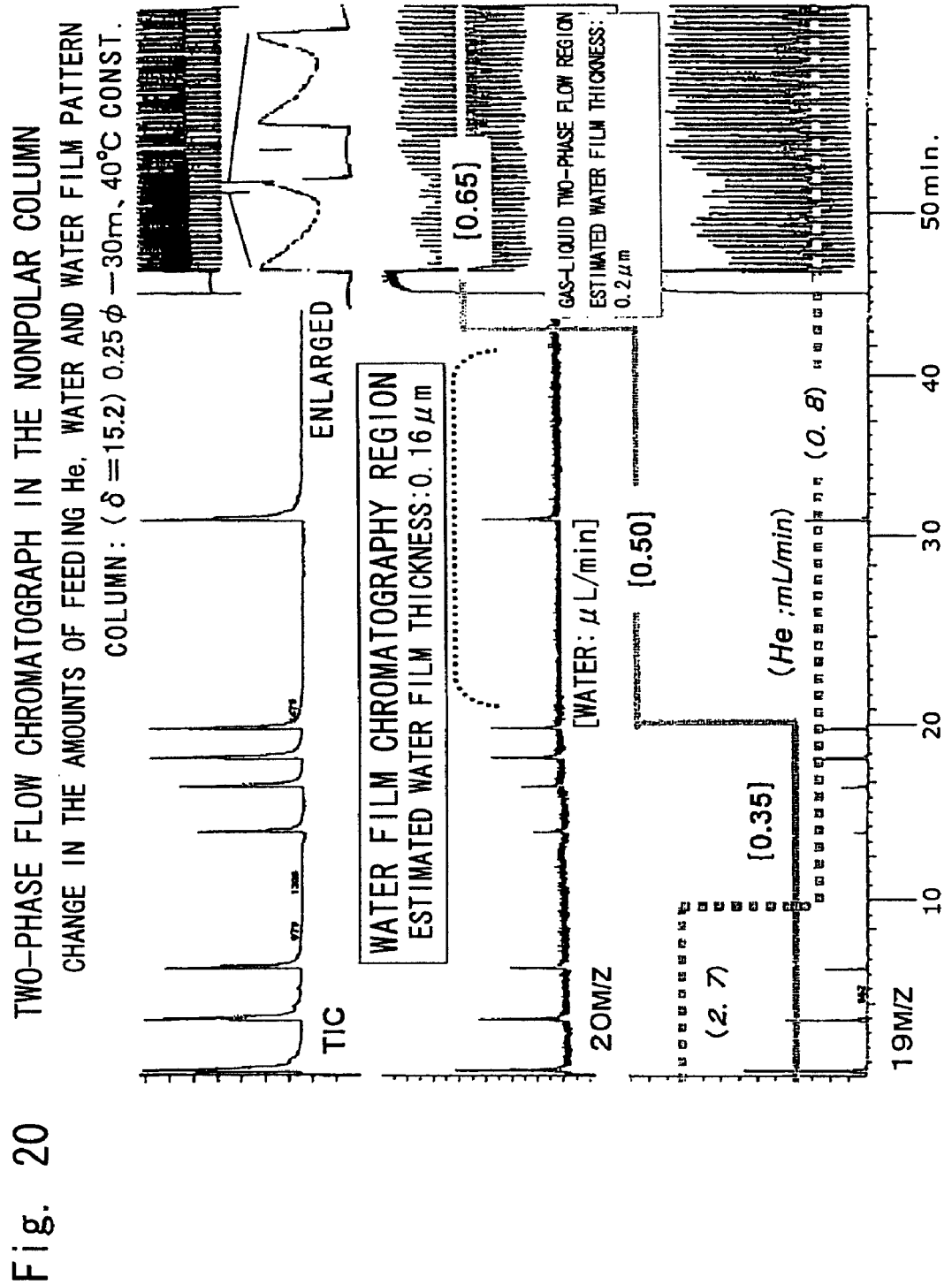
FIG. 20 is a diagram illustrating the results of analytical experiment in Example 9.

As shown in FIG. 20, the gas-liquid two-phase flow state was observed when water was fed at a rate of 0.65 μL/min., and the state where the water membrane chromatography could be applied was observed when water was fed at a rate of 0.5 μL/min. just preceding the above rate. It was observed that the carbonic acid gas dissolved again in water and simply foamed and bumped in a region of 0.35 μL/min. In the region where the gas-liquid two-phase flow was formed, the foaming contributed to forming stable and intermittent water masses.

The estimable water membrane thickness was calculated as follows:

TABLE 3

| Amount of water (μL/min.) | Amount of He (μL/min.) | holdup fraction 1-α | Estimable water film thickness (μm) |
|---|---|---|---|
| 0.35 | 2700 | 0.00013 | 0.033 |
| 0.50 | 800 | 0.00063 | 0.157 |
| 0.65 | 800 | 0.00081 | 0.203 |

Example 10

The capillary column solid phase resin for the gas chromatography is exclusively used for a silicone resin column. This is because the heat resistance inherent in the resin and the three-dimensional crosslinking technology of the coated material are providing a column of high performance. By using a siloxane compound containing a phenyl group or a cyano group for a copolymerizable monomer, it is allowed to obtain a silicone resin column having different polarity, and other resins have now been rarely used. The water membrane chromatography and the gas-liquid two-phase flow chromatography, however, use water as a separation medium. Therefore, hydrolyzing property of the silicone resin shortens the life of the column and is not desirable.

Polyisobutylene (PIB), polypropylene (PP), polystyrene (PS) and PTFE (polytetrafluoroethylene) which are general-purpose thermoplastic resins, were measured for their contact angles to estimate if they can be adopted for the gas-liquid two-phase flow chromatography. Table 4 shows the measured values of contact angles of water (n=3 on average) and solubility parameters (δ: MP$^{1/2}$)

TABLE 4

| Resin | (δ) | contact angle (deg) |
|---|---|---|
| PTFE (colored) | 14.5 | 105 |
| PTFE | 145 | 110 |
| PP | 17.2 | 72 |
| PS | 18.3 | 91 |
| PIB (tube) | 16.2 | 99 |
| PIB (film) | 16.2 | 106 |
| Dimethylsilicon | 15.2 | 96 |

Apparatus: DropMaster 700 manufactured by Kyowa Interface Science Co., Ltd.

The contact angles are all greater than 77° except the PP resin, and the polystyrene and polyisobutylene which are soluble in a solvent and can be turned into a three-dimensional form with a crosslinking agent, are highly probable to be used as a novel solid phase.

The polystyrene represents a numerical upper limit of properties of the solid phase resin for the gas-liquid two-phase flow chromatography. Therefore, the polystyrene capillary column was really prepared to examine its practicability.

A methyl ethyl ketone solution containing 0.1% of polystyrene was sucked under reduced pressure by a dimethylpolysiloxane (Df 0.1 μm) capillary column of a diameter of 0.1 mm and 10 meters long to fill it, and was gradually dried by ventilating the air. After drying, the solvent was removed by flowing He at 80° C. at a rate of 0.2 ml/min., and the capillary column was set in a GC oven.

The amount of application (Df) onto the column was estimated to be about 0.05 μm.

Figure 21:
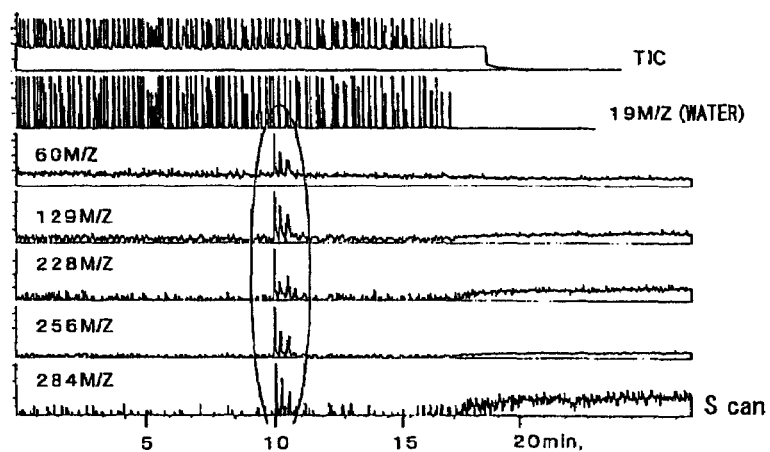
FIG. 21 is a diagram illustrating the results of analytical experiment in Example 10.
Figure 21:
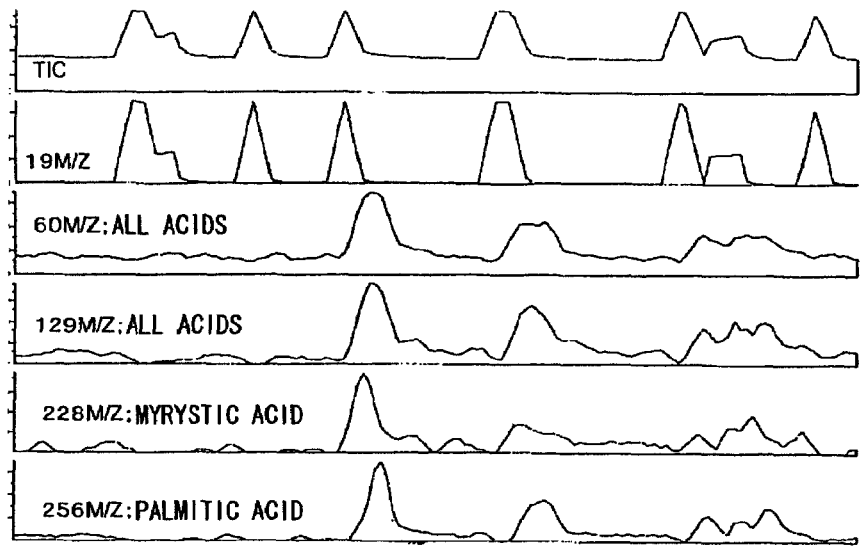

FIG. 21 shows a gas-liquid two-phase flow chromatography by the vaporization and condensation of water.

Sample: mixture of higher fatty acids (C14-C18 saturated fatty acids).

Column: Polystyrene was applied onto a 0.1 μm polydimethylsilicon column of a diameter of 0.10 mmφ and 10 meters long. Applied amount (Df) is estimated to be about 0.05 μm.

Condition: water 0.8 μL/min., He 0.2 mL/min.

MS: JEOL DX303 EI/MS 70 eV, 300 μA

Ultrasonic waves: not applied

Though three kinds of higher fatty acids have not been separated, it was confirmed that they were flowing out of the capillary column. The acids are separately developing as three sets probably because they are separately held by three water masses (plugs) being caused by the formation of unhomogeneously condensed water masses due to insufficient control in the method of vaporizing and condensing water.

In an enlarged diagram of FIG. 21(B), a fatty acid corresponding to a piece of water mass is observed maintaining a slight difference in the holding time suggesting a probability of separation if the intermittent period is sufficiently quick.

Example 11

The contact angle of water in a capillary column having silicone resin solid phase was measured by a two-dimensional IR imaging using an FT-IR microscope. The column possessed a diameter of 0.25 mmφ and was observed by injecting water in very small amounts. The contact angle of water can be calculated based on a relationship between the solubility parameter and the surface tension, and can be estimated to be,

LOG δ=1.19 (δ=15.6), LOG γ=1.32

∴20% phenyl: 80% methylsilicone resin, θ=86°

Figure 22:
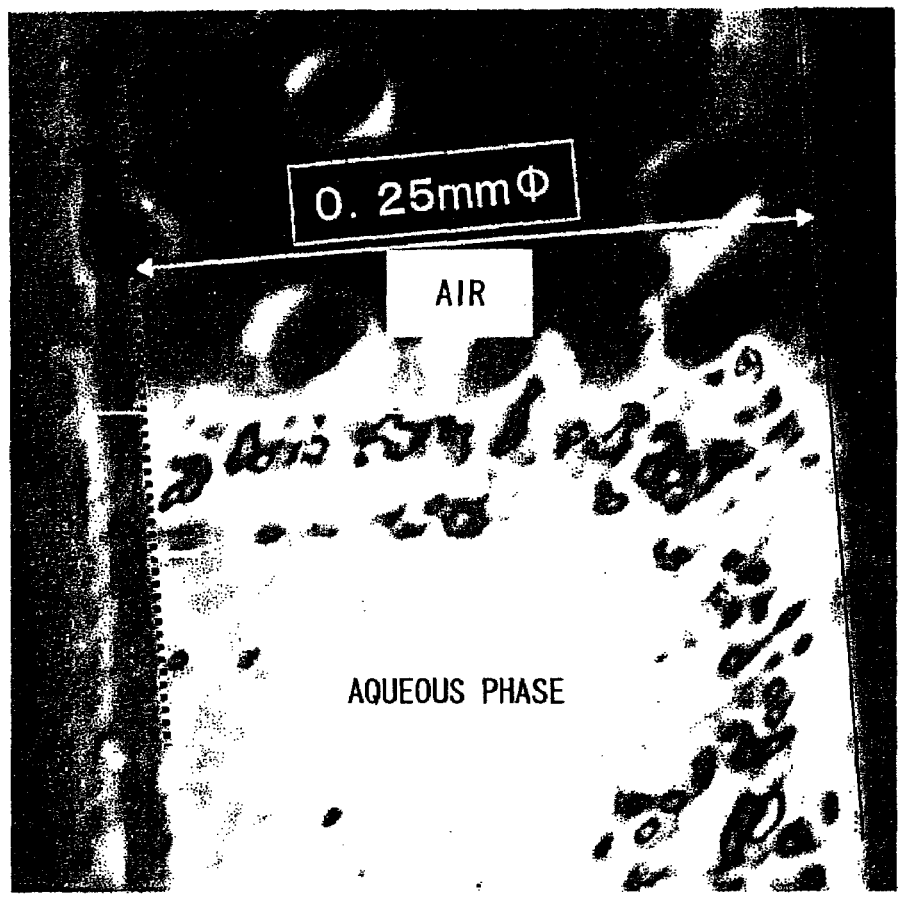
FIG. 22 is a diagram illustrating the results of measuring the interior of the capillary column by using an FT-IR microscopic two-dimensional IR imaging.

FIG. 22 is an imaging at 3958 cm$^{-1}$ by using an apparatus "STINGRAY" attached to the FT-IR, model FTS7000 manufactured by DEGILAB Co. The IR spectral absorption was large for the hydroxyl group possessed by water and by fused silica which is the material of the capillary column, most of the infrared rays passing through the tube was shut off, and the image could be drawn relying only upon part of the wavelengths of the hems of the peak.

According to the results of observing the interior of the capillary column in FIG. 22, the contact angle θ was 87° on the inner surface of the tube, which was in very good agreement with the contact angle 86° estimated from the properties of the resin for the column solid phase.

Example 12

By using a T-shaped flow path, the moving state of medium in the capillary column was turned into a two-phase flow state of moving phase media in which the carrier gas and the solvent, i.e., gas and liquid alternated intermittently.

In a tubular flow path of a very small inner diameter in which the carrier gas is introduced from one end, the solvent or the carrier gas containing the vapor thereof is introduced from another end, and a further end thereof is connected to the separation column, there is formed a two-phase flow state of moving phase media in which the air and liquid are intermittently alternating by forming closing portions for intermittent closure relying on the introduced solvent, and by eliminating the closing by conveying the closing solvent by using the carrier gas.

The T-shaped flow path was obtained by cutting a PEEK resin tube having an inner diameter of 0.4 mm and an outer diameter of 1/16 inches into a length of 20 mm, and perforating a through hole in the central portion of the tube by using a micro drill needle of 0.3 mm in diameter at right angles with the flow path of the PEEK tube. A SUS wire of a diameter of 0.3 mm was inserted in the hole at right angles with the tube. Capillary columns having an inner diameter of 0.15 mmφ coated with the dimethylsilicone resin were inserted in both ends of the PEEK tube up to the position of the SUS wire. Prior to inserting the columns, a polyimide resin solution was applied as a sealing agent onto the outer side surfaces and, after the insertion, was dried together with the column in an oven of 120° C. The SUS wire was carefully drawn such that an end thereof was at the center of diameter of the PEEK tube, a polyimide-coated fused silica capillary column blank tube coupled to a liquid feed pump for introducing the liquid in very small amounts was inserted until it contacted to the SUS wire and was fixed with an epoxy adhesive. The SUS wire was removed by about 0.15 mm which was one-half the inner diameter of the PEEK tube, and was fixed with an epoxy resin followed by heating and curing at 120° C. for 2 hours.

Figure 23:
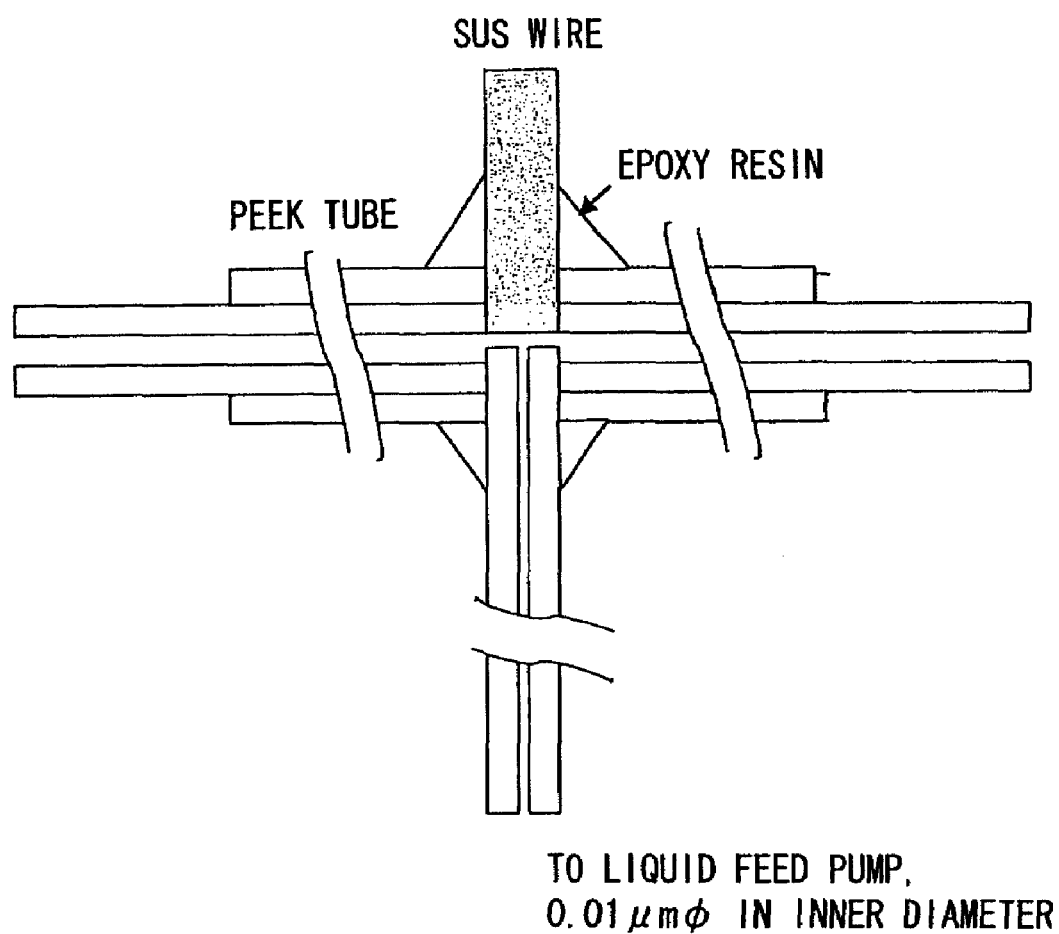
FIG. 23 is a diagram illustrating a T-shaped tube produced in Example 12.

It is estimated that the thus obtained T-shaped tube shown in FIG. 23 has a dead volume of 20 to 25 mL.

Figure 24:
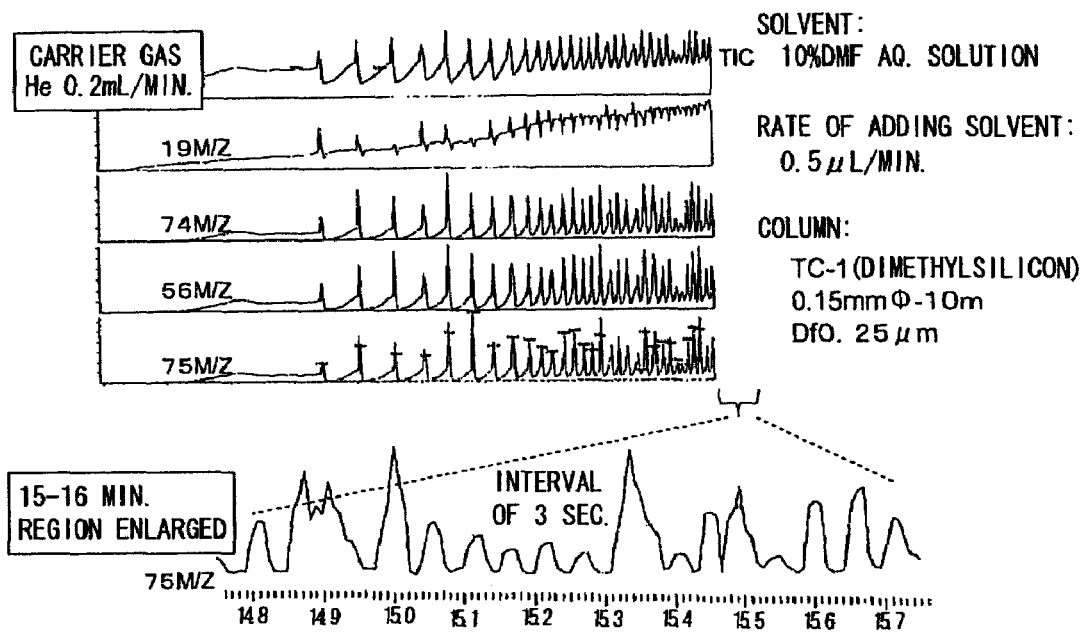
FIG. 24 is a diagram illustrating a state where the gas-liquid two-phase intermittent flow is formed in the T-shaped tube of FIG. 23.

FIG. 24 shows the state where the gas-liquid two-phase intermittent flow is formed by using the T-shaped tube shown in FIG. 23.

The carrier gas of He was fed at a rate of 0.2 mL/min. and the solvent of 10% dimethylformamide (DMF) was fed at a rate of 0.5 L/min. The column was coated with a nonpolar dimethylsilicone resin and possessed a length of 10 meters and an inner diameter of 0.15 mm.

The contact angle of an aqueous solution containing 10% of DMF was measured in the same manner as that of the above general-purpose resin to be θ=90° relative to the silicone rubber (the same material as the column). The silicone rubber has δ of 15.2 MPMP$^{1/2}$. Table 5 shows the contact angles for 10% DMF. When the organic solvent contains 10% of DMF, the contact angle decreases by 5 to 8° as compared to the case of water.

The occurrence of an intermittent flow is conformed from the chromatograph that shows a change in the amount of ions corresponding to the DMF in the MS detector; i.e., the intermittent flow becomes gradually stable and after 16 minutes have passed, the solvent assumes the state of plugs maintaining an interval of 3 seconds.

This experiment also made it sure that the gas-liquid two-phase flow chromatography can be conducted even by introducing the organic solvent blended with water by using a pump. If the scanning period (0.5 seconds) of the MS is further shortened, it is considered that the intermittent mountains and valleys can be clearly observed. In FIG. 24, however, the collection of data was not quick enough and mountains often appeared to be continuous to each other.

In FIG. 24, the peak intervals were measured to be gradually compressed. This is because since the GC apparatus is controlled to have a constant flow rate, an increase in the number of liquid phase plugs results in an increase in the resistance, and the alternating gaseous phase only is compressed.

Adjusting the gas-liquid alternating period is very important for controlling the state of the gas-liquid two-phase flow chromatography, and it was confirmed that the gas-liquid alternating interval could be varied by the flow rate/pressure control of the GC apparatus.

TABLE 5

| Resin | (δ) MP$^{1/2}$ | Contact angle water | Contact angle 10% DMF |
|---|---|---|---|
| PTFE (colored) | 14.5 | 105 | 100 |
| PTFE | 145 | 110 | 103 |
| PP | 17.2 | 72 | * |
| PS | 18.3 | 91 | * |
| PIB (tube) | 16.2 | 99 | * |
| PIB (film) | 16.2 | 106 | 98 |
| Dimethylsilicon | 15.2 | 96 | 90 |

Apparatus: DropMaster 700 manufactured by Kyowa Interface Science Co., Ltd.

Example 13

The gas-liquid two-phase flow chromatography can be constituted based on the gas chromatographic apparatus, and the detector, too, can be realized by using an EI-MS ion source which has been provided for GC/MS. This is because the void fraction in the column are as very high as 99% or more, which is substantially the same as a gas.

Figure 25:
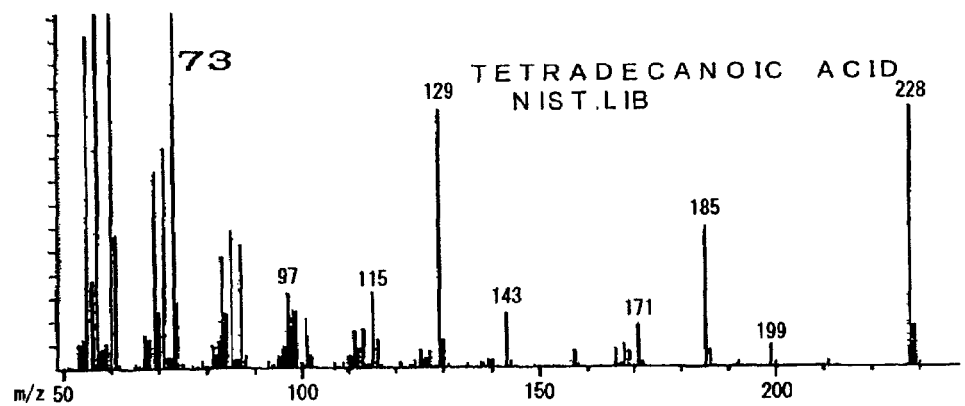
FIG. 25 is a diagram comparing the MS spectra in Example 10 with the standard spectra.
Figure 25:
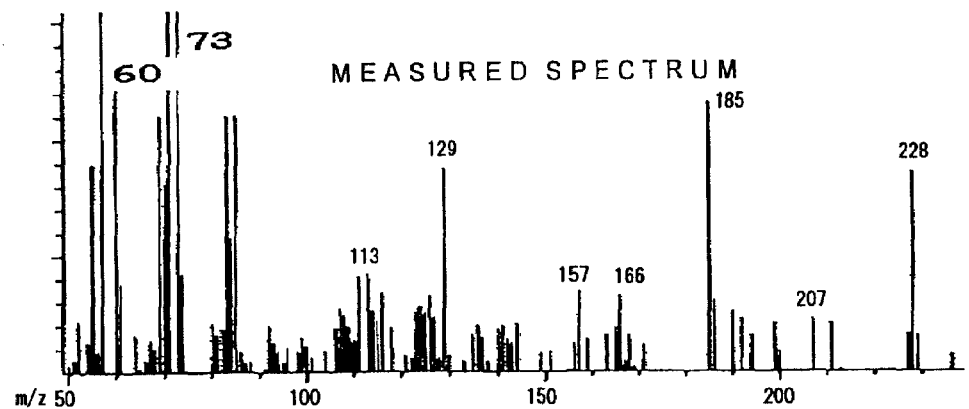
Figure 25:
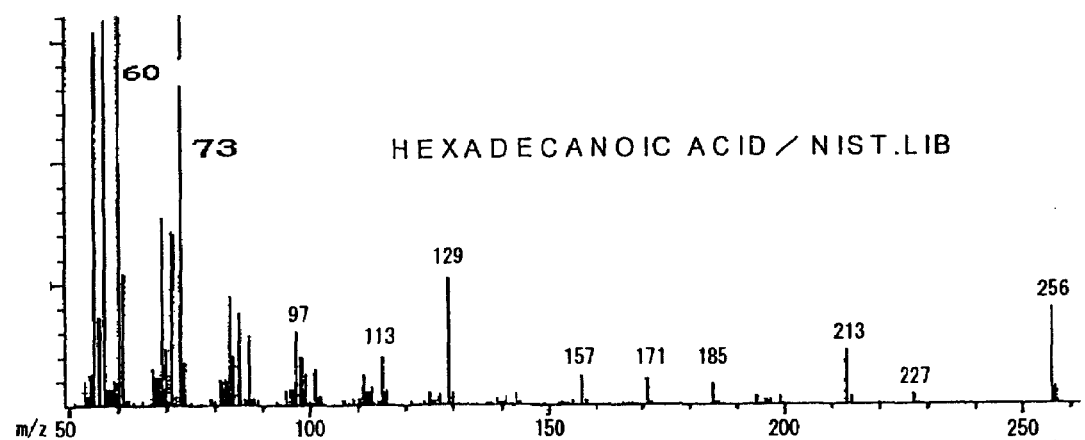
Figure 25:
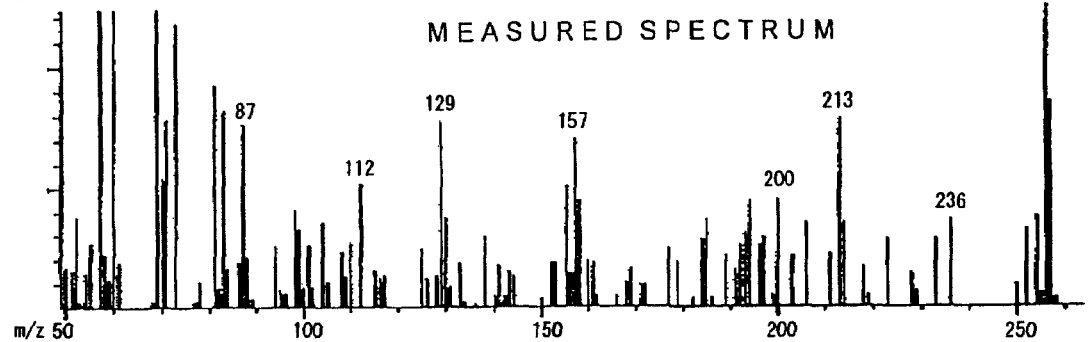

FIG. 25 shows MS spectra of the analysis of higher fatty acids using the styrene column of Example 10 above in comparison with the standard spectrum. The patterns are the same except the peaks of mixtures, and can be picked up by retrieving the NIST library.

The invention claimed is:

1. A gas-liquid two-phase flow chromatographic apparatus for the chromatographic analysis using a carrier gas as a main mobile phase medium and a polymer which is not miscible with water as a solid phase, and comprising at least a carrier gas introduction portion, a sample injection portion, a capillary column having a layer of the solid phase formed on the inner peripheral walls thereof, a container portion thereof and a detection portion; wherein said sample injection portion is provided between said carrier gas introduction portion and the inlet of the capillary column, and includes medium introduction means capable of adding and mixing a liquid solvent as a second mobile phase medium to said carrier gas, a mechanism for controlling the amount of introducing said carrier gas and the amount of adding said mobile phase solvent, and a mechanism for controlling the temperatures of the flow paths in which the two mobile phase media come in contact; and wherein said analyzer is so constituted that the portions of the apparatus and the control mechanism are interlinked together in a manner that the liquid membrane thickness partly forms a plurality of manometric liquid plugs in the separation column which is in operation in the radial direction of the capillary and in the lengthwise direction of the column maintaining an interval, that the mobile phase media move toward the outlet of the column in a state where the gas phase and the liquid phase are intermittently alternating, and that the chromatographic analysis is conducted while executing the separation and developing by utilizing the distribution of the solvent membrane of the mobile phase media and the column solid phase.

2. The gas-liquid two-phase flow chromatographic apparatus according to claim 1, wherein the solvent membrane in the capillary column in the apparatus which is in operation has an average value of the estimated liquid membrane thickness in a unit time (1 unit: shorter than 10 seconds) in a range of not smaller than 0.1 μm as calculated according to the following formula (I), $$\text{Average value (μm) of the estimated liquid membrane thickness in a unit time} = \text{inner diameter of column (mm)} \times (1-\alpha) \times 10^3 \quad (1)$$

wherein α is a ratio represented by (flow rate of gaseous volume/flow rate of the volume of the whole fluid) of the fluid in the capillary column under the atmospheric pressure, and the length of interval between the manometric liquid plugs detected at the outlet of the column is not longer than 10 seconds as a liquid pulse interval time measured by a mass analyzer.

3. The gas-liquid two-phase flow chromatographic apparatus according to claim 1, wherein a wet contact angle between the liquid solvent which is said second mobile phase medium and the solid phase material in said capillary column is not smaller than 77°.

4. The gas-liquid two-phase flow chromatographic apparatus according to claim 3, wherein the liquid solvent in said capillary column is water, and the solid phase material is a high molecular resin or a resin composition having a solubility parameter value (SP-value or δ-value) of not higher than 18.3 MPa$^{1/2}$.

5. The gas-liquid two-phase flow chromatographic apparatus according to claim 3, wherein the liquid solvent in said capillary column is water, and the surfaces of the solid phase material are so treated as to exhibit surface property of a solubility parameter value of not higher than 18.3 MPa$^{1/2}$.

6. The gas-liquid two-phase flow chromatographic apparatus according to claim 3, wherein said liquid solvent is a mixed solution of water and an organic solvent.

7. The gas-liquid two-phase flow chromatograph apparatus according to claim 3, wherein said liquid solvent is organic solvent.

8. The gas-liquid two-phase flow chromatographic apparatus according to claim 3, wherein said liquid solvent is a mixed solution of organic solvents.

9. The gas-liquid two-phase flow chromatographic apparatus according to claim 1, wherein the solvent introduction means which adds and mixes the solvent as the second mobile phase medium to said carrier gas, works to heat, vaporize and continuously introduce the solvent at an average liquid flow rate of 0.01 to 2 μL/min, and, thereafter, condense and liquefy the solvent, so that a state of a two-phase flow of mobile phase media in which the gas and the liquid are intermittently alternating is established in the capillary column in which an average value of the estimated liquid membrane thickness in a unit time is not smaller than 0.1 μm.

10. The gas-liquid two-phase flow chromatographic apparatus according to claim 1, wherein the solvent introduction means which adds and mixes the solvent as the second mobile phase medium to said carrier gas, continuously introduces the solvent at an average liquid flow rate of 0.01 to 2 λm/min. by using a liquid feed pump, so that a state of a two-phase flow of mobile phase media in which the gas and the liquid are intermittently alternating is established in the capillary column in which an average value of the estimated liquid membrane thickness in a unit time is not smaller than 0.1 μm.

11. The gas-liquid two-phase flow chromatographic apparatus according to claim 10, wherein means that establishes a state of a two-phase flow of mobile phases in which the gas and the solvent are intermittently alternating in the capillary column, is a tubular flow path which introduces the carrier gas from one end thereof and introduces the solvent or the carrier gas containing the vapor thereof from the other end thereof, the end on the outlet side of the confluent path thereof being connected to the separation column, and the tubular flow path is further provided with a capillary portion of an inner diameter small enough to be closed by the liquid solvent or the condensate of the solvent vapor that is introduced, the tubular flow path further having a solvent flow rate adjusting mechanism for alternately repeating a step of forming closing membranes or masses of the solvent introduced into the capillary portion and a step of eliminating the closing by conveying the closing portions with the carrier gas, and a carrier gas flow rate-adjusting mechanism, wherein the alternating interval is adjusted by the cooperative operations thereof to realize the state of two-phase flow of mobile phase media in which the gas and the liquid are intermittently alternating.

12. The gas-liquid two-phase flow chromatographic apparatus according to claim 1, further comprising a mechanism that gives sonic vibration to said capillary column.

13. The gas-liquid two-phase flow chromatographic apparatus according to claim 1, wherein a mass analyzer is used as said detector.

14. The gas-liquid two-phase flow chromatographic apparatus according to claim 1, wherein a hydrogen flame ionization detector is used as said detector.

15. The gas-liquid two-phase flow chromatographic apparatus according to claim 1, wherein as the solid phase in said separation column, there is used a styrene resin and a polyisobutylene resin, an olefin resin having a branched methyl group, such as a 4-methylpentene resin, or a three-dimensionally crosslinked product thereof.

16. A composite chromatographic analyzing method using a carrier gas as a main mobile phase medium and a polymer which is not miscible with water as a solid phase by using a chromatographic analyzer comprising at least a carrier gas introduction portion, a sample injection portion, a capillary column having a layer, of the solid phase formed on the inner peripheral walls thereof, a container portion thereof, a detection portion and means capable of adding water, water vapor or an organic solvent to said carrier gas, said composite chromatographic analyzing method comprising the steps of:

A) introducing a gas comprising chiefly the carrier gas into said capillary column to separate and develop volatile components in a sample to be analyzed that is injected in a gas-solid gas chromatographic state;

B) separating and developing chiefly polar component materials by adding and mixing a predetermined amount of water, water vapor or both of them to the carrier gas so as to form a water membrane of nearly a constant thickness having an average value of the estimated liquid membrane thickness in a unit time of 0.01 to 0.09 μm on the surface of the solid phase in said capillary column; and C) separating and developing the component materials that are difficult to be separated and developed in said steps A) and B) above by adding and mixing a predetermined amount of liquid solvent capable of forming a solvent membrane of an average value of the estimated liquid membrane thickness in a unit time of not less than 0.1 μm in the separation column as a second mobile phase medium to the carrier gas which is the first mobile phase medium, and by moving the mobile phase media toward the outlet of the column in a state where the solvent membrane is partly forming a plurality of manometric liquid plugs in the radial direction of the capillary column and in the lengthwise direction in the column maintaining an interval in the separation column, the gas phase and the liquid phase intermittently alternating.

\* \* \* \* \*